United States Patent
Chuter et al.

(10) Patent No.: US 7,708,771 B2
(45) Date of Patent: *May 4, 2010

(54) ENDOVASCULAR GRAFT DEVICE AND METHODS FOR ATTACHING COMPONENTS THEREOF

(75) Inventors: Timothy A. M. Chuter, Atherton, CA (US); Matthew J. Fitz, Sunnyvale, CA (US); Robin W. Eckert, San Jose, CA (US); Vivianne M. Holt, San Jose, CA (US); Tina Ton, San Jose, CA (US); Octavian Iancea, Fremont, CA (US); Juan I. Perez, Sunnyvale, CA (US); Richard Newhauser, San Francisco, CA (US); Shuji Uemura, San Mateo, CA (US); David T. Pollock, San Carlos, CA (US); Reid Hayashi, Palo Alto, CA (US); George Caffell, Moss Beach, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/090,492

(22) Filed: Mar. 4, 2002

(65) Prior Publication Data
US 2003/0176912 A1 Sep. 18, 2003

Related U.S. Application Data

(60) Provisional application No. 60/360,323, filed on Feb. 26, 2002.

(51) Int. Cl.
*A61F 2/82* (2006.01)
*A61F 2/86* (2006.01)
(52) U.S. Cl. .................. 623/1.13; 623/1.14; 623/1.36

(58) Field of Classification Search ............... 623/1.13, 623/1.14, 1.36, 1.35; 606/191, 192, 198, 606/200

See application file for complete search history.

(56) References Cited

U.S. PATENT DOCUMENTS

| | | | |
|---|---|---|---|
| 2,030,791 A * | 2/1936 | Hickok | 3/326 |
| 4,562,596 A | 1/1986 | Kornberg | |
| 5,562,724 A | 10/1996 | Vorwerk et al. | |
| 5,575,817 A | 11/1996 | Martin | |
| 5,639,278 A | 6/1997 | Dereume et al. | |
| 5,686,451 A | 11/1997 | Kristianson et al. | |
| 5,713,917 A | 2/1998 | Leonhardt et al. | |
| 5,957,974 A | 9/1999 | Thompson et al. | |
| 6,051,020 A | 4/2000 | Goicoechea et al. | |
| 6,099,558 A * | 8/2000 | White et al. | 623/1.16 |
| 6,102,940 A * | 8/2000 | Robichon et al. | 623/1.35 |
| 6,120,522 A | 9/2000 | Vrba et al. | |
| 6,162,246 A | 12/2000 | Barone | |

(Continued)

FOREIGN PATENT DOCUMENTS

WO  WO 98/32399  7/1998

*Primary Examiner*—Anhtuan T Nguyen
*Assistant Examiner*—Amy T Lang
(74) *Attorney, Agent, or Firm*—Brooks, Cameron & Huebsch, PLLC

(57) ABSTRACT

The present invention embodies an endovascular graft having various frame-to-main body component attachment mechanisms which provide a secure bond, reduced graft material wear, and reduced delivery profile.

29 Claims, 24 Drawing Sheets

U.S. PATENT DOCUMENTS 6,280,466 B1 * 8/2001 Kugler et al. .............. 623/1.12
6,368,345 B1 * 4/2002 Dehdashtian et al. ...... 623/1.13
6,652,580 B1 * 11/2003 Chuter et al. .............. 623/1.36
7,090,693 B1 * 8/2006 Chobotov et al. .......... 623/1.13

* cited by examiner

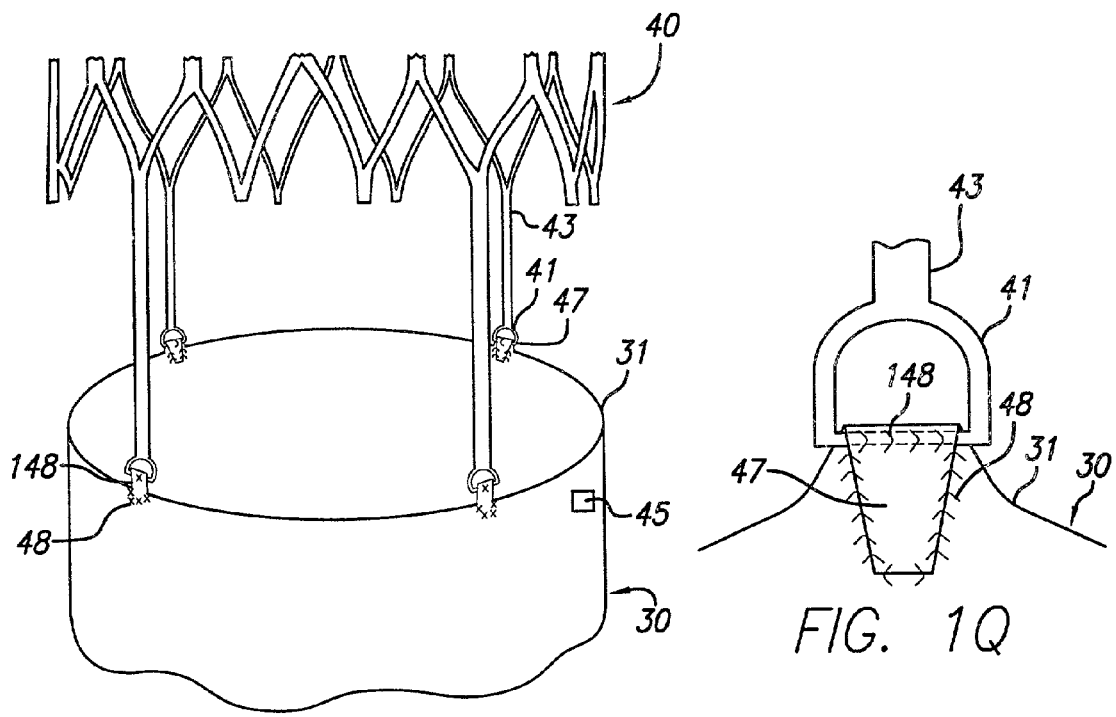
FIG. 1P
FIG. 1Q
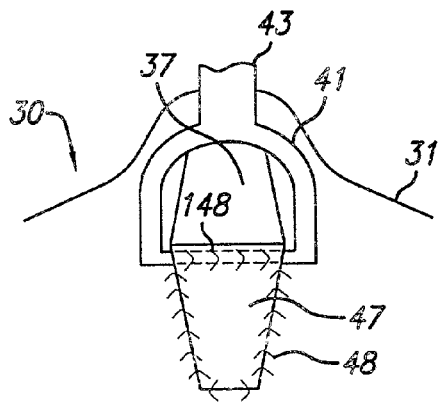
FIG. 1R
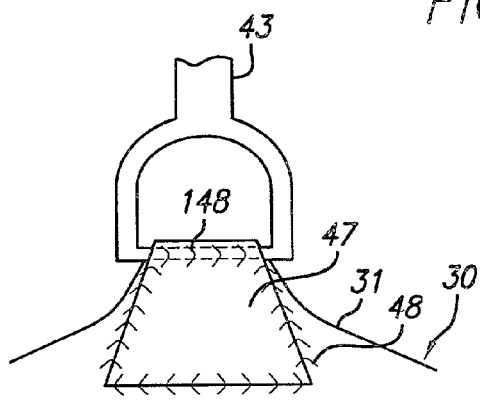
FIG. 1S
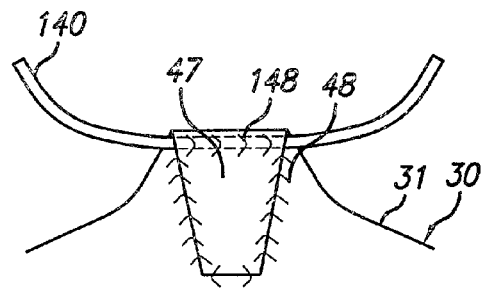
FIG. 1T

ENDOVASCULAR GRAFT DEVICE AND METHODS FOR ATTACHING COMPONENTS THEREOF

This application claims the benefit of U.S. Provisional Application Ser. No. 60/360,323, filed Feb. 26, 2002, entitled Endovascular Grafting Device, which contents are incorporated herein by reference in their entirety.

BACKGROUND OF THE INVENTION

This invention relates to an endovascular graft assembly for treating vasculature of a patient and more specifically to graft system and the attachment of structures thereof.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids and, in turn, may be life threatening. In some cases, the damage to the lumen is repairable only with the use of prosthesis such as an artificial vessel or graft.

For repair of vital lumens such as the aorta, surgical repair is significantly life threatening or subject to significant morbidity. Surgical techniques known in the art involve major surgery in which a graft resembling the natural vessel is spliced into the diseased or obstructed section of the natural vessel. Known procedures include surgically removing the damaged or diseased portion of the vessel and inserting an artificial or donor graft portion inserted and stitched to the ends of the vessel which were created by the removal of the diseased portion. More recently, devices have been developed for treating diseased vasculature through intraluminal repair. Rather than removing the diseased portion of the vasculature, the art has taught bypassing the diseased portion with a prosthesis and implanting the prosthesis within the vasculature. An intra arterial prosthesis of this type has two components: a flexible conduit, the graft, and the expandable framework, the stent (or stents). Such a prosthesis is called an endovascular graft.

It has been found that many abdominal aortic aneurysms extend to the aortic bifurcation. Accordingly, a majority of cases of endovascular aneurysm repair employ a graft having a bifurcated shape with a trunk portion and two limbs, each limb extending into separate branches of vasculature. Currently available bifurcated endovascular grafts fall into two categories. One category of grafts are those in which a preformed graft is inserted whole into the arterial system and manipulated into position about the area to be treated. This is a unibody graft. The other category of endovascular grafts are those in which a graft is assembled in-situ from two or more endovascular graft components. This latter endovascular graft is referred to as a modular endovascular graft. Because a modular endovascular graft facilitates greater versatility of matching the individual components to the dimensions of the patient's anatomy, the art has taught the use of modular endovascular grafts in order to minimize difficulties encountered with insertion of the devices into vasculature and sizing to the patient's vasculature.

Although the use of modular endovascular grafts minimize some of the difficulties, there are still drawbacks associated with the current methods. Drawbacks with current methods can be categorized in three ways; drawbacks associated with delivery and deployment of the individual endovascular graft components, drawbacks associated with the main body portion, and drawbacks associated with securing the limb portions to the main body portion.

The drawbacks of current methods of delivery and deployment of endovascular graft components include redundant components for delivery, delivery of both a graft and its securing stent as a single entity, and at least minor surgery in order to gain access to the vasculature of the patient. In some systems, current methods for delivering the individual components of a modular endovascular graft to the treatment site require the use of a separate delivery catheter for each component and exchange of the delivery catheters through an introducer sheath after each component has been deployed. There are a number of disadvantages to this method. Since each delivery catheter has to be smaller than the introducer sheath, this limits the design of the implant, makes packing the implant into the delivery system more difficult, and increases the force required to deploy the implant. The use of multiple delivery catheters increases production costs and decreases reliability due to the multiplicity of catheter parts required. The process of removing one delivery system and replacing it with another may require coordination between two operators to ensure that guidewire access is maintained, a longer guidewire, additional procedure time, a large amount of physical space, and additional trauma to the insertion and delivery sites.

Furthermore, the known methods for delivering grafts to the required location within a patient's vascular system also require that an attachment system be delivered simultaneously with the graft, axially overlapping the graft and located either on the interior or the exterior of the graft's lumen, so that upon deployment of the graft the attachment system is expanded to attach the graft to the vascular wall. The attachment system is typically connected to the graft before implantation in the patient by means such as stitching. As a consequence, the outer diameter of the delivery capsule or sheath containing the compressed graft is increased by the presence of the compressed attachment system. Complications may be encountered in maneuvering the compressed graft and its delivery system around the bends and branches of the patient's vascular system. It will be appreciated that the greater the outer dimension of the capsule containing the compressed graft to be delivered, the more inflexible it will be, making delivery to the final destination more difficult and perhaps even impossible in some patients.

Moreover, in the majority of cases, the patient must be subject to surgery in which the appropriate vessel is surgically exposed and opened by incision to allow entry of the graft. Significantly, it is this surgical procedure on the vessel which can give rise to serious complications such as infection, patient discomfort, and necrosis of the vessel itself. However, if the outside dimension of the delivery capsule were sufficiently small, it might be possible, depending on the size and condition of the patient, to insert the capsule into the patient's vessel by applying sufficient force to the skin and artery of the patient with a sharpened end of the graft's delivery capsule, similar to the commonly known method of inserting a needle directly into the vein or artery of a patient.

With regard to the method of delivery and deployment of endovascular graft components, there therefore exists a need for a stent-graft delivery system that limits the amount of redundancy of delivery components required, can be easily operated by a single technician without decreased reliability or additional risk to the patient, facilitates a reduced outside dimension of the capsule or sheath containing a compressed graft component to be delivered to the patient's vascular system, and minimizes the need for surgery in order to gain entry to the patient's vasculature.

The drawbacks of current embodiments of the main body component of a modular endovascular graft include a larger delivery profile due to the aforementioned graft and supporting stent as a single entity as well as additional stents within the separate branches of a bifurcated main body portion, difficulty in catheterizing the connection site of the first endovascular graft component prior to introduction of the second endovascular graft component, and a lack of adequate healthy tissue near the aneurysm for anchoring the graft to the aortic wall. Although the prior art has taught that the larger delivery profile of a combined graft and supporting stent can be minimized by providing separate support stents for the trunk and limb support branches of the main body component rather than a single support stent for the entire main graft component, separate support stents for the limb support branches are conventionally located at the same axial level. This results in a larger delivery profile since the support stents, when collapsed for delivery, lie on top of each other.

Furthermore, because of the restricted geometry of the vasculature and the small diameter of the limb supporting branch of the main body component, it can be difficult to insert one element of a modular endovascular graft into another. The instrumentation required to insert catheters and deploy the limb components of a modular endovascular graft inside the main graft limb support sections can dislodge mural thrombus in the AAA. The dislodged mural thrombus is carried in the blood flow through the femoral arteries to small distal arteries causing blockage and tissue necrosis.

Moreover, a lack of healthy tissue near the aneurysm being treated provides difficulty with adequately anchoring the main body portion of a modular endovascular graft. If the aneurysm is too close to the renal arteries there may be a lack of healthy tissue to adequately anchor the neck of the main graft portion without interfering with blood flow in the renal arteries. Anchoring the limb support branches of the main body component in the iliac arteries requires a larger main body component and additional effort and delivery hardware. Allowing the limb support branches of the main body component to float freely in the aneurysm presents other difficulties with deploying the limb components of the modular endovascular graft within the main body component.

With regard to the main body component of modular endovascular graft, there therefore exists a need for a main body component that facilitates a minimized delivery profile, easier catheterization of the limb support portions and accurate deployment of the limb components, and anchoring of the neck portion near the renal arteries without disrupting cross-blood flow.

The devices and methods of the present invention address these and other needs.

SUMMARY OF THE INVENTION

Briefly and in general terms, the present invention is embodied in an endovascular graft system composed of various components and the attachment of the components to a graft device.

Throughout this specification, the term "proximal" shall mean "nearest to the heart", and the term "distal" shall mean "furthest from the heart." Additionally, the term "ipsi-lateral" shall mean the side for example of the limb of a bifurcated graft which is deployed using the same path through the vasculature that was used to deploy the main body component, and the term "contra-lateral" shall mean the side for example of the limb of a bifurcated graft which is deployed using a second path through the vasculature which is catheterized after the main body component has been deployed. Furthermore, the term "inferior" shall mean "nearest to the technician", and the term "superior" shall mean "farthest from the technician."

In one aspect, the invention is a main body component of a modular endovascular graft with an attachment frame, for example, a self-expanding attachment stent at its proximal end that is secured to the neck portion of the main body graft by hanging attachment arms, a stabilized trunk portion that resists twisting, and limb support portions that facilitate accurate catheterization and deployment of the limb components. Axial separation of the attachment stent from the main body graft of a modular endovascular graft allows anchoring the attachment stent above the renal arteries without disturbing blood flow into the renal arteries from the aorta and facilitates a reduced delivery profile since the stent and graft do not occupy the same axial location when compressed in the delivery system. By using hooks or a combination of stent eyelets and short sutures which connect the stent hanging attachment rings to the main body graft by engaging reinforced holes at the proximal end of the neck portion, the delivery profile is further reduced by avoiding suture knots which can add bulk to the graft in the delivery system. Another advantage of knot-less attachments is a reduction in the possibility of suture fatigue failures over the life of the graft. The delivery profile can be further reduced by eliminating unnecessary graft material between the reinforced holes at the proximal end of the neck portion, a process known as "scalloping". Varying the length of the stent hanging connection rings and their associated connection hooks or sutures further reduces the delivery profile by limiting the number of hooks or eyelets which occupy the same axial location when the stent is compressed in the delivery system. Eyelets at the proximal end of the attachment stent facilitate its compression and loading into the loading capsule of the preferred embodiment delivery system.

If there is sufficient healthy tissue, additional self-expanding stents can be located at the proximal end of the neck portion and the distal end of each limb support portion. In order to minimize the delivery system profile, these stents can be delivered separately from the main body component. Stability of the main body component can be enhanced by a "U-shaped" wire in the main body graft which resists twisting.

Catheterization of the limb support portions of the main body component and accurate deployment of the limb components is facilitated by several features. Additional self-expanding attachment or support stents can be added to stabilize the main body component and hold the limb support portions open. These stents impact the delivery profile less than a full main body graft support stent and the impact can be minimized by making the limb support portions different lengths so their stents do not occupy the same axial location when the main body component is compressed in the delivery catheter. Furthermore, the limb support portions may be sutured together from the crotch to the distal end of the shortest limb support portion to resist twisting. Moreover, the catheterization of the limb support portion and delivery and deployment of the limb component to the contralateral side can be further facilitated by adding a bell-bottom endovascular graft section to the distal end of the contralateral limb support portion. By extending the bell-bottom stent longitudinally into the contralateral limb support section, a sufficient docking portion can be provided even if the bell-bottom endovascular graft becomes bent due to the configuration of the vasculature. By making the perpendicular profile of the distal end of the bell-bottom endovascular graft oval with respect to the body and the distal edge nearest the aneurysm wall significantly longer than the inner distal edge, the landing surface area can be increased further.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1P is a partial perspective view of the area designated by the dotted lines in FIG. 1 showing an alternate embodiment of the invention with the attachment stent attached to the main body component by tabs of graft material;

FIG. 1Q is a partial elevational view depicting a graft tab formed as part of the graft material that is inserted through a connector eyelet and sutured to the main body component graft material;

FIG. 1R is a partial elevational view depicting a graft tab cut out of the graft material that is inserted through a connector eyelet and sutured to the main body component graft material;

FIG. 1S is a partial elevational view depicting an alternate embodiment of the graft tab shown in FIG. 1Q;

FIG. 1T is a partial elevational view depicting a graft tab folded over a bent wire stent and sutured to the main body component graft material;

FIG. 1AA is a partial perspective view of the area designated by the dotted lines in FIG. 1, depicting a "scalloped" graft superior end;

DETAILED DESCRIPTION OF THE PREFERRED EMBODIMENTS

The present invention relates to an endovascular graft and structure and methods for attaching and securing the individual components thereof.

Figure 1:
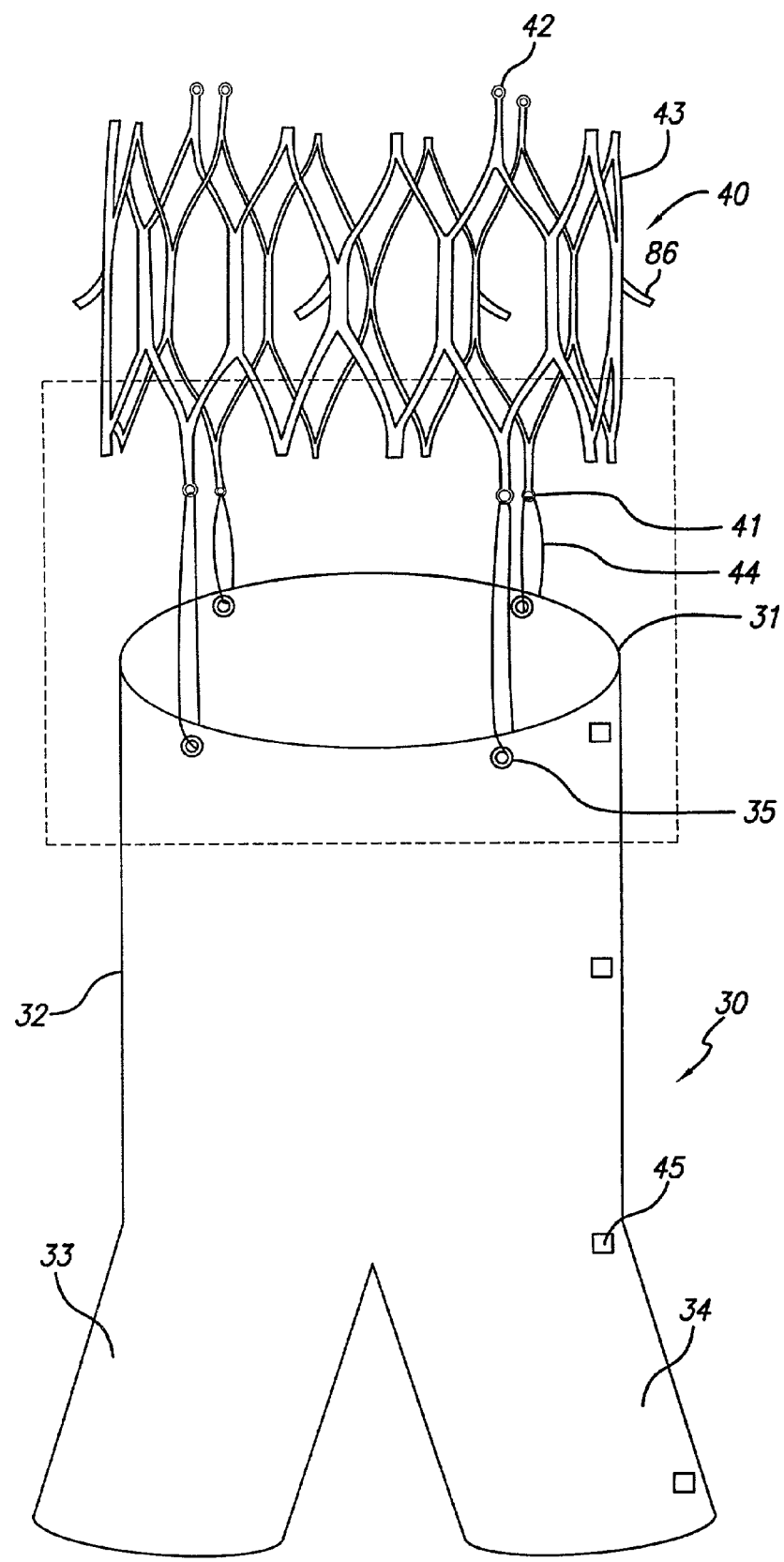
FIG. 1 is a perspective view, depicting a bifurcated endovascular graft main body component and attachment stent in accordance with one embodiment of the present invention.

FIG. 1 shows the main body component 30 and attachment stent 40 of a bifurcated endovascular graft that is one aspect of the present invention. The main body component 30 consists of a superior end or neck 31, trunk 32 and two limb support portions 33, 34. The limb support portions 33, 34 facilitate insertion, deployment, and attachment of limb components of the modular endovascular graft. Radiopaque markers 45 placed along the contra-lateral side of the graft material identify the neck 31, mid-point, bifurcation, and distal end of the contra-lateral limb support portion 34, thereby facilitating placement within the patient's body.

The anchoring or attachment stent 40 includes an expandable frame 79 and has connector eyelets 41 at its distal end, loading eyelets 42 at its proximal end, and attachment hooks or barbs 86 at its midpoint. The attachment stent 40 connector eyelets 41 and connector holes 35 in the proximal end of the neck 31 facilitate attaching the main body component 30 to the attachment stent 40. Note that the location of the connector holes 35 as shown is for demonstration purposes only. It is contemplated that connector holes 35 may be located at alternate locations around the circumference of the neck 31 of the main body component 30 in order to facilitate packing of the main body component 30 and attachment stent 40 for delivery in a catheter. The attachment stent 40 loading eyelets 42 facilitate loading the attachment stent 40 into the delivery system catheter. The attachment stent 40 attachment hooks or barbs 86 facilitate anchoring the stent 40 in the lumen wall and prevent migration of the attachment stent 40 and attached main body component 30.

The attachment stent 40 is preferably self-expanding and maybe laser cut from Nitinol or a similar material. Note that the connector eyelets 41 and loading eyelets 42 are offset longitudinally from the rest of the stent struts 43. This longitudinal offsetting facilitates a smaller delivery profile as the circumferentially-wider eyelets 41, 42 occupy a different axial position than the rest of the struts 43 when the stent 40 is packed for delivery in a delivery system catheter, thereby allowing greater compression of the stent 40. The eyelets 41, 42 may also be offset longitudinally from each other to further facilitate compression of the stent 40 (see FIG. 8). In a preferred embodiment, the loading eyelets 42 have a diameter of 0.025 inches and are equally spaced 90 degrees apart to support the insertion of two stainless steel wires or fishing lines which are used to collapse the stent to a very low profile and then be pulled into a sheath of a delivery system.

Figure 1A:
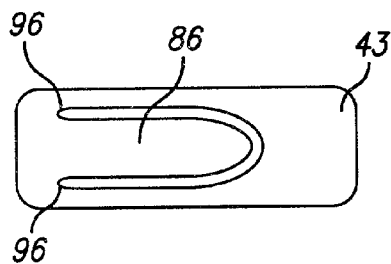
FIG. 1A is a top view of a stent hook depicting cutout, critical strain locations.
Figure 1B:
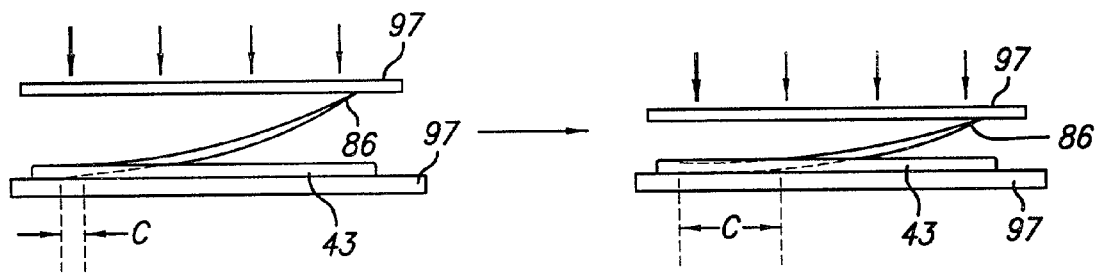
FIG. 1B is a side view depicting a curved hook being compressed for delivery by a mandrel.

To reduce strain on the attachment hooks 86 when they are packed for delivery, they are curved. FIG. 1A depicts a typical attachment hook 86 generally representing the embodiments of the present invention and indicates cutout critical strain locations 96, the area where the hook 86 is projecting from the attachment stent 40 strut 43. When the hook 86 is compressed for delivery, it bends at the critical strain locations 96 and stress damage may occur. Referring to FIG. 1B, a curved attachment hook 86 is shown being compressed for delivery by a delivery sheath or collapsing tool over a mandrel or catheter inner member 97. The curvature of the hook 86 creates a contact area between the hook 86 and underlying mandrel (indicated as C) that acts as a fulcrum to reduce that strain to the cutout critical strain locations 96. Unlike a straight hook, which does not have contact with the underlying mandrel, the curved hook 86 is exposed to less strain during packing and, therefore, has a lower risk of breaking. The attachment hook or barb 86 may be made from any self-expanding material, such as Nitinol or Elgiloy. The radius of the hook 86 may be adjusted to maximize the strain reduction effect and its angle with respect to the stent 40 may be adjusted to provide optimal placement in the aortic wall. It is contemplated that the hook 86 may be manufactured as an integral part of the stent 40 or may be welded/attached to the stent 40 after manufacture. It is further contemplated that curved attachment hooks or barbs 86 may be utilized in other stents, such as additional main body 30 support stents (see FIG. 3A).

Figure 1C:
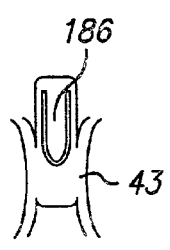
FIG. 1C is a partial elevational view depicting a stent with a unidirectional single hook.
Figure 1D:
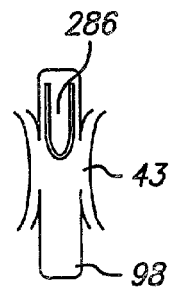
FIG. 1D is a partial elevational view depicting a stent with a uni-directional single hook with a tail.
Figure 1E:
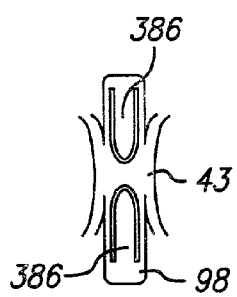
FIG. 1E is a partial elevational view depicting a stent with bi-directional hooks and a tail.
Figure 1F:
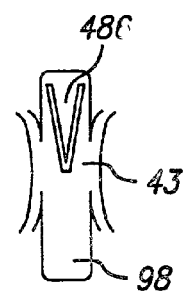
FIG. 1F is a partial elevational view depicting a stent with a tapered uni directional single hook and a tail.

The shape and direction of the attachment hooks 86 may be selected to provide optimal fixation within the lumen. FIG. 1C depicts an embodiment of a single attachment hook or barb 186 facing the distal direction, which is the direction of blood flow. The flow of blood will help embed the hook 186 in the lumen wall. FIG. 1D depicts an attachment hook 286 with a tail portion 98. The tail portion 98 increases the force with which the hook 286 contacts the lumen wall by reducing the amount of bending or rotation of the top of the hook 286 toward the center of the lumen away from the lumen wall. Such rotation tends to reduce the force with which the attachment hook 286 contacts the lumen wall, thereby resulting in less penetration and a weaker seal. FIG. 1E depicts an embodiment of bi-directional attachment hooks 386 which resist the tendency of the distally facing hook 386 to dislodge if the stent 40 is accidentally moved in the proximal direction by subsequent interventional procedures by a physician. FIG. 1F depicts a tapered attachment hook 486 which facilitates penetration of the lumen wall. It is contemplated that the shape and direction of the hooks or barbs may be varied to improve attachment anytime axial fixation of a component is desired.

Figure 1G:
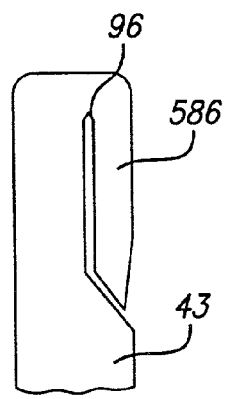
FIG. 1G is a partial elevational view depicting an alternate hook design of the present invention.
Figure 1H:
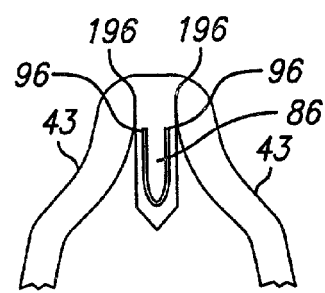
FIG. 1H is a partial elevational view depicting an alternate hook location of the present invention.

The location of the attachment hooks 86 with respect to the stent strut 43 may also be altered to provide better fatigue performance and optimal fixation within the lumen. FIG. 1G depicts an embodiment of attachment hook or barb 586 cut at the edge of the stent strut 43. Note that the number of critical strain locations 96 is reduced by a factor of two and the stent support strut 43 is thicker. The extent of laser cutting required to cut the hook is reduced and the fatigue characteristics are enhanced, thereby reducing the probability of cracks occurring or growing. FIG. 1H depicts a hook or barb 86 placed between the stent struts 43 just below a strut junction. Note that the critical strain locations 96 of the hook 86 and stent strut 43 junction 196 are separated. Placing the hook 86 near the top of the stent 43 facilitates shortening the overall length of the stent 43. Furthermore, the radial force applied by the stent 43 to the hook 86 is increased since the force created by the stents pushing against each other, which is near the top of the stent 43 junction, is close to the hook 86 location.

Figure 1I:
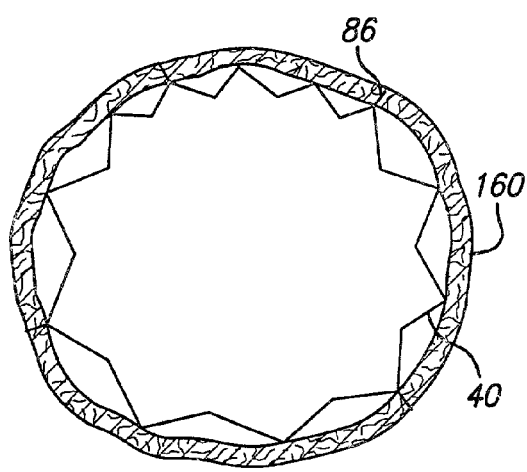
FIG. 1I is a cross-sectional top view depicting an attachment stent with 4 hooks deployed asymmetrically within a body lumen.

Additionally, limiting the number of attachment hooks 86 (for example, 2 or 3) may improve stent 40 expansion and improve fixation in some circumstances. Referring to FIG. 1I, the irregular shape of the patient's vasculature 160 may result in some of the attachment hooks 86 imbedding prior to others, with the resultant asymmetrical expansion of the stent 40.

Figure 1J:
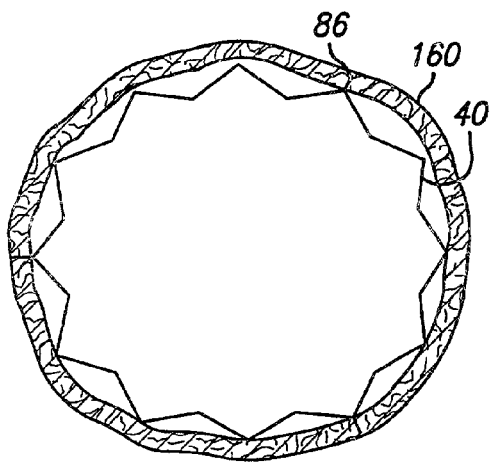
FIG. 1J is a cross-sectional top view depicting an attachment stent with 3 hooks deployed symmetrically within a body lumen.

Referring to FIG. 1J, decreasing the number of attachment hooks 86 lessens the likelihood of asymmetrical expansion. In other circumstances given the high loads (about 3 to 5 newtons) present on the hooks due to blood flow, a larger number of hooks, for example, 6 to 12 are desirable.

One embodiment of attaching the attachment stent 40 to the main body component 30 utilizes loops or hooks. As shown in FIG. 1, a metal link or suture is used to form a connector loop 44 which is threaded through a connector eyelet 41 of the attachment stent 40 and a connector hole 35 in the neck 31 of the main body component 30. The length of the connector loop 44 can vary from a short length, such that the neck 31 of the main body component 30 abuts the distal end of the attachment stent 40, to a long length sufficient to allow deployment of the attachment stent 40 proximal the renal arteries with the neck 31 of the main body component 30 located distal the renal arteries.

Figure 1K:
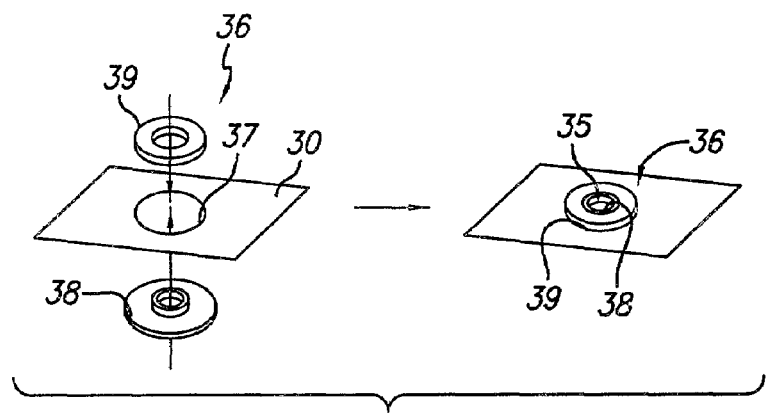
FIG. 1K is a partial perspective view depicting a grommet used to reinforce the connector holes.

To reduce wear and damage to the graft material of the main body component 30, the connector holes 35 maybe reinforced. As shown in FIG. 1K, one embodiment of the invention for reinforcing the connector holes 35 is to use a grommet 36. A die (not shown) is used to make a graft hole 37 which is then reinforced by pressing together two hollow plastic or metal rings 38, 39. An alternative method for reinforcing the connector holes 35 is to sonically cut and treat them.

Figure 1L:
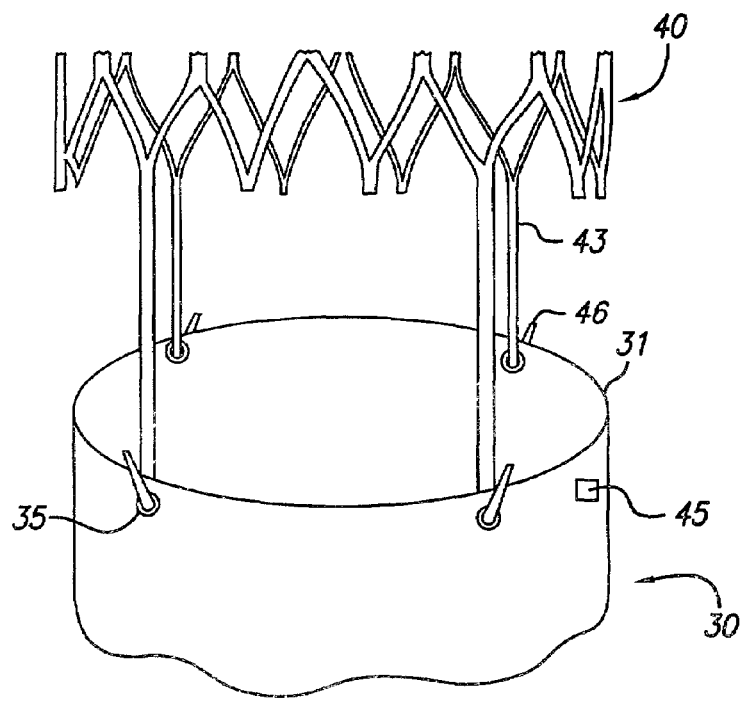
FIG. 1L is a partial perspective view of the area designated by the dotted lines in FIG. 1 showing an alternate embodiment of the invention with the attachment stent attached to the main body component by hooks.

FIG. 1L depicts an embodiment of the invention illustrating the use of hooks to attach the attachment stent 40 to the main body component 30. The attachment stent 40 has extended struts 43 with connector hangers or hooks 46 at the distal end. The connector hangers 46, which are angled toward the proximal direction, either pierce the graft material or are attached to connector holes 35 in the neck 31. When deployed, the main body component 30 hangs from the attachment stent 40 by the hangers 46.

Figure 1M:
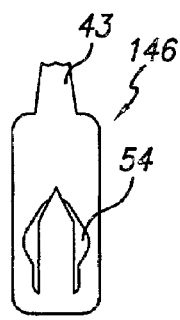
FIG. 1M is a partial elevational view depicting a stent connector hanger with a sharp distal edge and widened cutout.
Figure 1N:
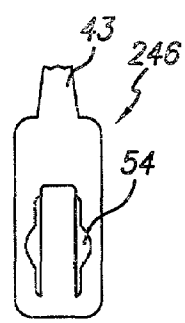
FIG. 1N is a partial elevational view depicting a stent connector hanger with a rounded distal edge.
Figure 1O:
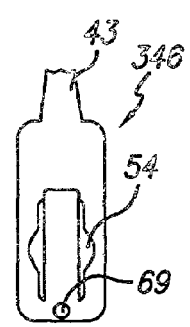
FIG. 1O is a partial elevational view depicting a stent connector hanger with a suture hole.

FIG. 1M depicts an embodiment of connector hanger 146 with a sharp edge to facilitate piercing the graft material. Note that the connector hanger 146 cutout 54 is widened near the midpoint of the hangers to allow the graft material to more easily surround the connector hanger 146 and, thereby, minimize graft wear. FIG. 1N depicts a connector hanger 246 with a rounded edge to facilitate engaging a connector hole 35 without tearing the graft material. FIG. 1O depicts an embodiment of a connector hanger 346 with a suture hole 69 at the distal end that facilitates attaching the connector hanger 346 to the graft material for additional support.

The length of the stent strut 43 to which the connector hanger 46 is attached can vary from a short length, such that the neck 31 of the main body component 30 abuts the distal end of the attachment stent 40, to a long length sufficient to allow deployment of the attachment stent 40 proximal the renal arteries with the neck 31 of the main body component 30 located distal the renal arteries. In a preferred embodiment, the hangers 46 are made of Nitinol.

An alternate embodiment for attaching the attachment stent 40 to the main body component 30, shown in FIG. 1P, utilizes portions of graft material that are inserted through the attachment stent 40 connector eyelets 41 and sutured to the main body component 30 graft material. The attachment stent 40 connector eyelets 41 are shaped to allow a tab 47 of graft material to pass through. Each graft material tab 47 is inserted through a connector eyelet 41 and secured to the graft material at the neck 31 of the main body component 30. By attaching the tab 47 to graft material by sutures 48 or other means, the strength of the bond between the attachment stent 40 and main body component 30 is defined by the strength of the graft material, a bond that can be stronger than just a few sutures used to attach the stent 40 to the graft material. Additional reinforcing sutures 148 may be used to secure the connector eyelet 41 to the tab 47.

The main body component 30 graft material maybe cut with tabs 47 at the neck 31, as shown in FIG. 1Q, or tabs 47 may be formed by cutting holes 37 in the graft material of the neck 31, as shown in FIG. 1R. The shape of the tab may be varied in order to provide a wide area of attachment to the main body component 30 graft material as shown in FIG. 1S. The joint between the stent 40 and graft material tab 47 may be strengthened further by suturing patterns that distribute the load of the stent 40 more evenly (see FIGS. 2A to 2D).

It is contemplated that graft tabs 47 may also be utilized with a bent-wire stent 140, as shown in FIG. 1T, whereby the tab 47 is inserted through the bend apex of the stent 140 and secured to the main body component 30 graft material. It is further contemplated that this method may be used anytime it is desired to attach a stent to a graft.

Figure 1U:
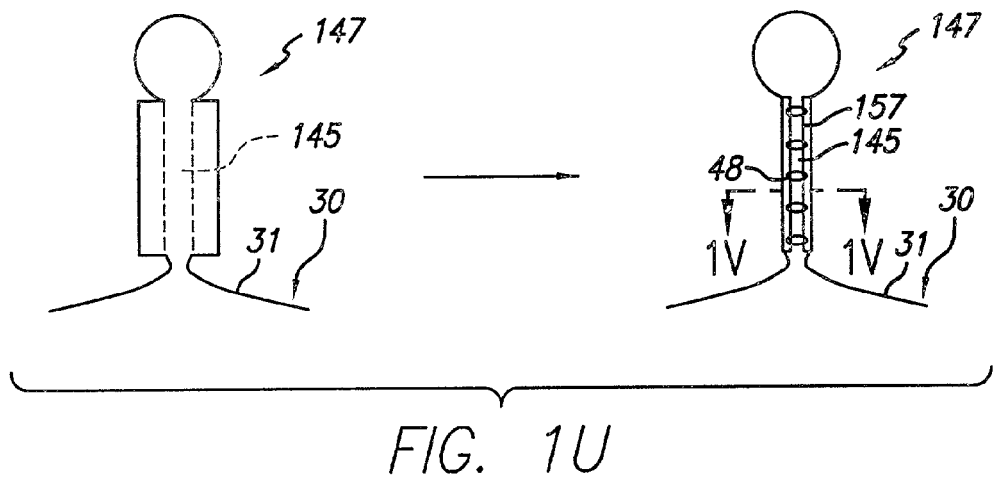
FIG. 1U is a partial elevational view depicting the midpoint a graft tab reinforced by folding the graft material along foldlines and suturing.
Figure 1V:
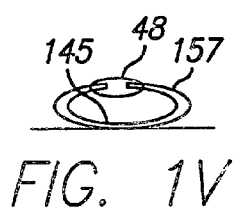
FIG. 1V is a cross-sectional view along line IV-IV of FIG. of 1U depicting the reinforcing graft material.
Figure 1W:
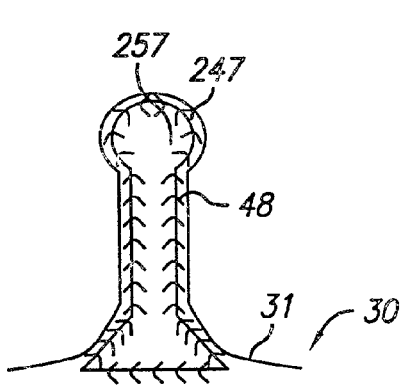
FIG. 1W is a partial elevational view depicting a graft tab reinforced by suturing a second portion of graft material to it.

The strength of the graft material tab 47 may be increased by additional layers of graft material. FIGS. 1U and 1V show embodiments of a graft material tab 147 whose midsection 145 is folded along foldlines (indicated by dotted lines) and sutured 48 together to form a second layer of graft material 157. The second layer of graft material 157 distributes the longitudinal load of the stent 40 among more vertical threads and thereby increases the breaking and fatigue strength of the junction as well as resistance to abrasion. FIG. 1W shows an embodiment of a graft material tab 247 to which an additional layer of graft material 257 has been bonded by sutures 48. Special fibers within the graft material or treatment of the graft material with polymers or other chemicals may also add strength to the tab 47.

Figure 1X:
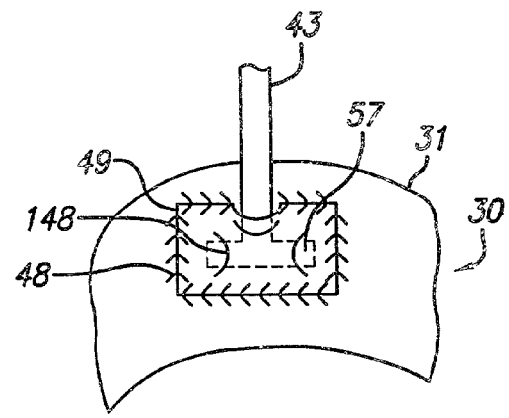
FIG. 1X is a partial elevational view depicting a stent bulb captured by a graft patch sutured to the main body component graft material.

Another alternate embodiment for attaching the attachment stent 40 to the main body component 30, shown in FIG. 1X, utilizes struts 43 with areas of increased width, or connector bulbs 57, at the proximal end. The connector bulbs 57 are captured in graft pockets 49 formed by portions of graft material placed over the connector bulbs 57 and attached to the main body component 30 by sutures 48 such that only a small area where the stent strut 43 enters the graft pocket 49 is unsecured. The connector bulbs 57, which may be "T" shaped, are sufficiently wider than the stent struts 43 such that they cannot slip out of the graft pockets 49. The graft-to-graft bond is more reliable than traditional suture joints between stent 40 and graft. As with previously defined graft tab methods, additional reinforcing sutures 148 maybe used to secure the connector bulbs 57 to the graft material and the bond between the patches 49 and graft material may be strengthened by suturing patterns that distribute the load of the stent 40 more evenly (see FIGS. 2A to 2D). It is contemplated that this method may be used anytime it is desired to attach a stent 40 to a graft. It is contemplated that this method may be utilized with a bent-wire stent 140, as shown in FIG. 1Y, whereby the graft patch 149 is attached to the main body component 30 graft material by sutures 48 such that only two small areas where the stent 40 enters and exits the graft pocket 149 are unsecured.

Figure 1Z:
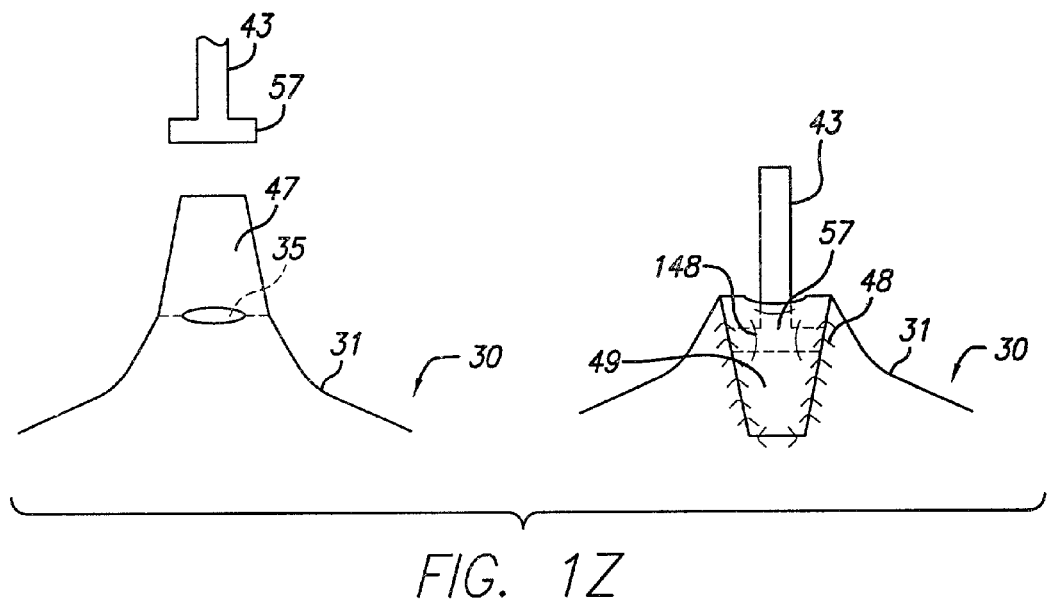
FIG. 1Z is a partial elevational view depicting a bulb inserted through a connector hole in a graft tab which is sutured to the main body component graft material.
Figures 1A, 1Y:
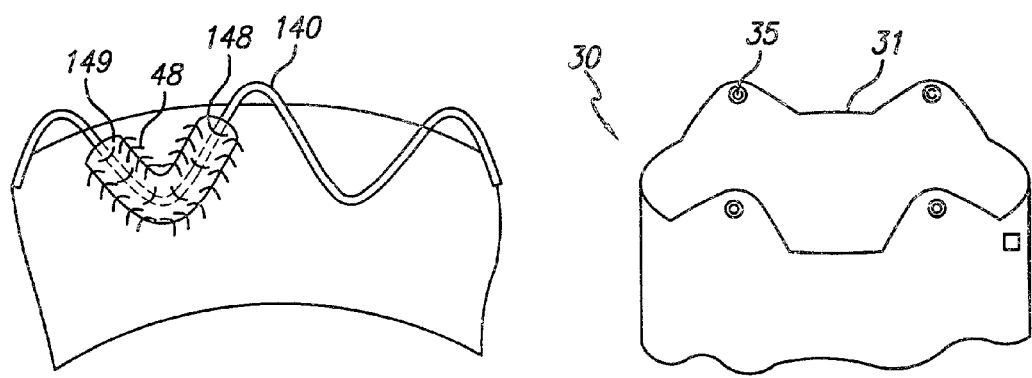
FIG. 1Y is a partial elevational view depicting a bent-wire stent captured by a graft patch sutured to the main body component graft material.

Another alternate embodiment of attaching the attachment stent 40 to the main body component 30, shown in FIG. 1Z, incorporates main body component 30 graft tabs 47 and an attachment stent 40 having connector bulbs 57 at the proximal end. Connector holes 35 are cut in the main body component 30 graft material at fold points (indicated by the dotted line) at the base of the graft tabs 47. The attachment stent 40 connector bulbs 57 are inserted into the connector holes 35 and the graft tabs 47 folded over at the foldpoints and sutured 48 to the main body component 30 graft material, thereby forming graft material pockets 49 which capture the attachment stent 40 connector bulbs 57. As with previously defined graft tab 47 methods, additional reinforcing sutures 148 may be used to secure the connector bulbs 57 to the graft material and the bond between the patches 49 and graft material may be strengthened by suturing patterns that distribute the load of the stent 40 more evenly (see FIGS. 2A to 2D).

Reducing the amount of graft material that must be compressed and packed into a catheter sheath further reduces the delivery system profile. Referring to FIG. 1AA, a process called "scalloping" is utilized to remove unnecessary graft material between the connector holes 35 at the neck 31 of the main body component 30. This process obtains a reduced delivery profile even if traditional suture methods are used to attach the attachment stent 40 to the main body component.

Figure 2:
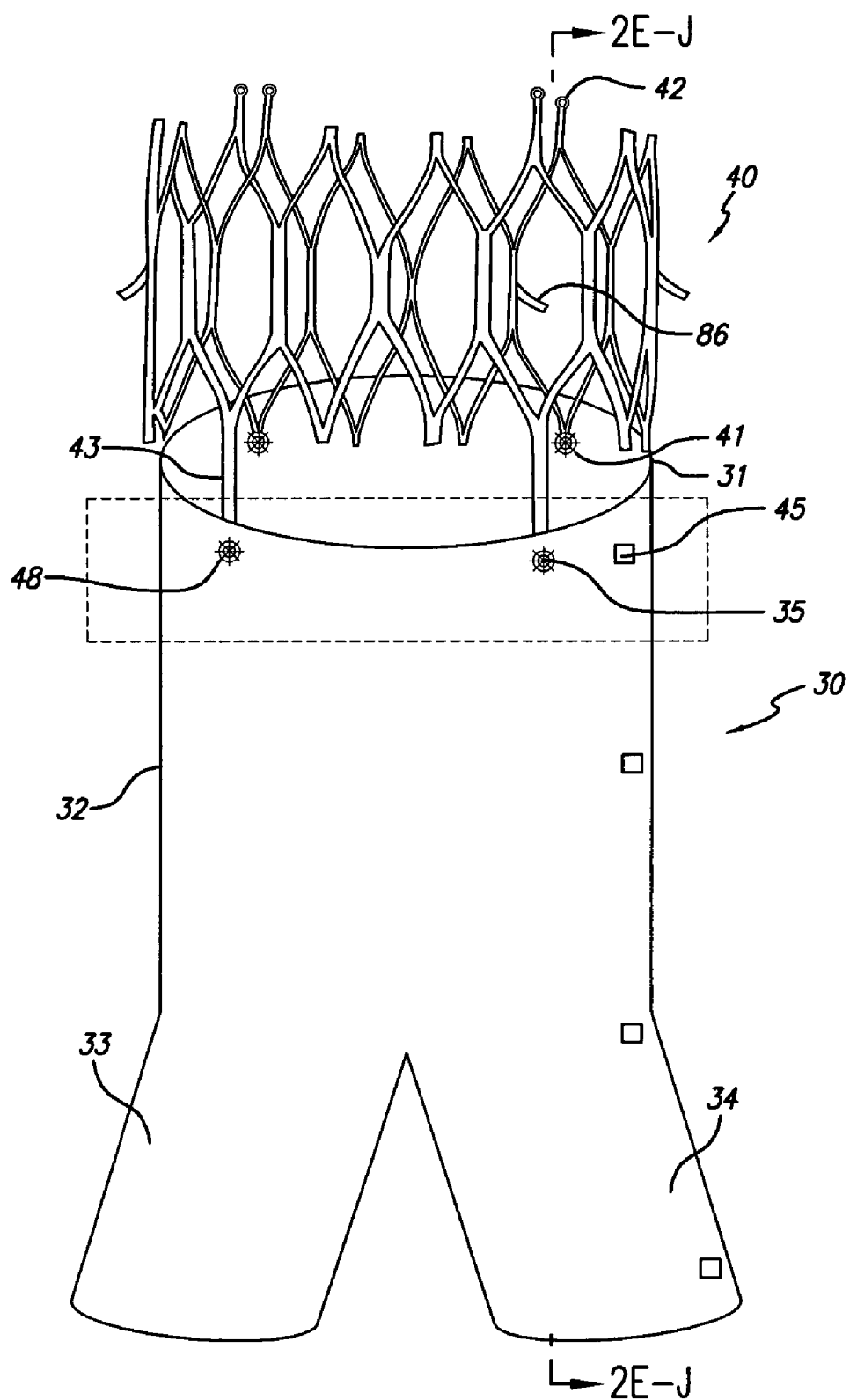
FIG. 2 is a perspective view of an alternate embodiment of the bifurcated endovascular graft main body component and attachment stent depicted in FIG. 1 with the attachment stent sutured directly to the graft material of the main body component.

Another alternate method for attaching the attachment stent 40 to the main body component 30, shown in FIG. 2, utilizes improved methods to suture the stent 40 directly to the neck 31 of the main body component 30. The suturing techniques ensure a more reliable joint that resists tearing of the graft material. Providing a larger radius edge at the contact point between the suture 48 and connector eyelets 41 improves the durability of the junction by reducing stresses on the suture 48 material.

As shown in FIGS. 2A-2D, spoke-like, radial suture patterns and running stitches 65 in the graft fabric having multiple tie-offs or knots 61 (designated by the black dots in the figures) are used to attach the connector eyelets 41 directly to the connector holes 35 of the main body component 30. The tie-offs or knots 61 help transfer the load from the sutures 48 to the graft material and prevent excessive gathering or bunching of the graft material fabric. This suturing technique distributes the attachment stent 40 forces over a greater area and provides redundancy, thereby ensuring a more reliable joint. It is contemplated that these suturing techniques may be used anytime it is desired to attach a stent to graft material.

Figure 2A:
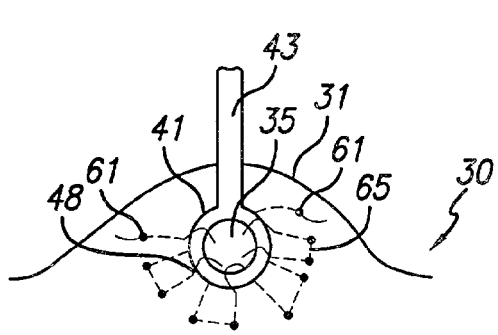
FIG. 2A is a partial elevational view of the area designated by the dotted lines in FIG. 2, depicting a stent connector eyelet sutured to the connector hole with running stitches between each suture material loop.
Figure 2B:
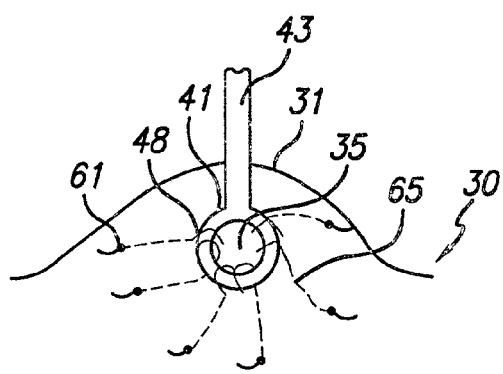
FIG. 2B is a partial elevational view of the area designated by the dotted lines in FIG. 2, depicting a stent connector eyelet sutured to the connector hole with a running stitch approach and break away for every two to four suture loops.
Figure 2C:
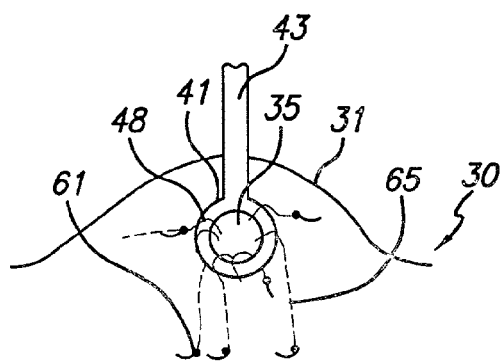
FIG. 2C is a partial elevational view of the area designated by the dotted lines in FIG. 2, depicting a stent connector eyelet sutured to the connector hole with one short running stitch approach and a long running stitch and knot break away for every two to four suture loops.
Figure 2D:
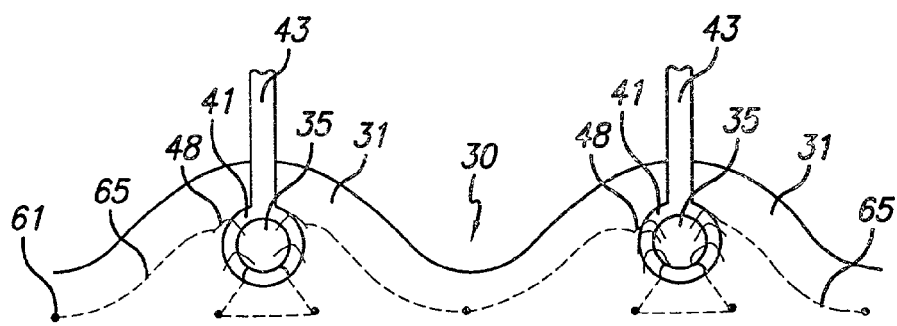
FIG. 2D is a partial elevational view of the area designated by the dotted lines in FIG. 2, depicting a stent connector eyelet sutured to the connector hole with a running stitch between attachment points that follows the scalloped edge of the main body component and a running stitch triangular pattern with knots for every 2 to 4 loops beneath each attachment point.

FIG. 2A shows an embodiment having running stitches 65 between each suture loop 48 which threads through an attachment stent 40 connector eyelet 41 and main graft body 30 connector hole 35. Note that there is a suture knot or tie-off 61 at the beginning and end of a single running stitch 65 which connects all the suture loops 48 for a single connector eyelet 41. FIG. 2B shows a variation with a running stitch 65 approach and running stitch 65 "break away" for every two to four suture loops 48. Note that there are suture knots 61 for every two to four suture loops 48 such that a single suture 48 break will not cause a complete failure of the joint between the eyelet 41 and main graft body 30. FIG. 2C shows another variation with a short running stitch 65 approach and a long running stitch 65 "break away" for every two to four suture loops 48 that attach the connector eyelet 41 to the graft material of the main body component 30. FIG. 2D shows another variation with a running stitch 65 between connector eyelets 41 that follows the scalloped edge of the main body component 30 neck 31 and a running stitch 65 triangular pattern for every 2 to 3 suture loops 48 beneath each connector eyelet 41. Note that there are multiple suture knots 61; at midpoints between connector eyelets 41 along the running stitch 65 and at each corner of the triangular patterns.

By providing a large radius cross-section at the contact point between the attachment stent 40 connector eyelet 41 and each suture loop 48, the bending stress and abrasion caused by loading the suture material is reduced. Reducing these stresses increases the durability of the joint between the attachment stent 40 and graft material. It is contemplated that this method may be used anytime it is desired to attach a metallic stent to graft material.

Figure 2E:
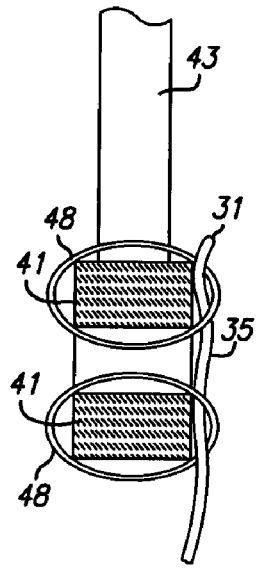
FIG. 2E is a partial cross-sectional view along the line 2E-J-2E-J of the area designated by the dotted lines in FIG. 2, depicting a stent eyelet having a cross-section with sharp corners.
Figure 2F:
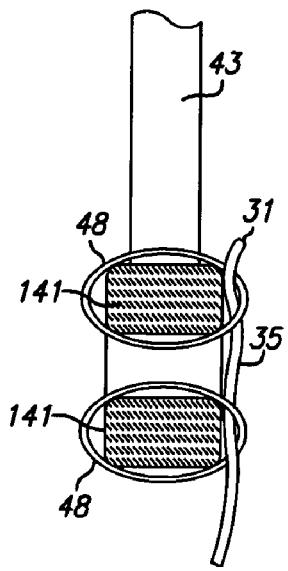
FIG. 2F is a partial cross-sectional view along the line 2E-J-2E-J of the area designated by the dotted lines in FIG. 2, depicting a stent eyelet having a cross-section with round corners.

FIG. 2E shows a typical attachment stent 40 connector eyelet 41 having a cross-section with sharp edges. When the sutures 48 are pulled tight around the eyelet 41, the sharp corners cause stress that degrades the material over time. Suture 48 failure may eventually occur. FIG. 2F shows an embodiment of an attachment stent 40 connector eyelet 141 having a cross-section with rounded edges. The rounded edges provide a large radius which will cause less stress to the material of the sutures 48 when they are pulled tight around the eyelet 141.

Figure 2G:
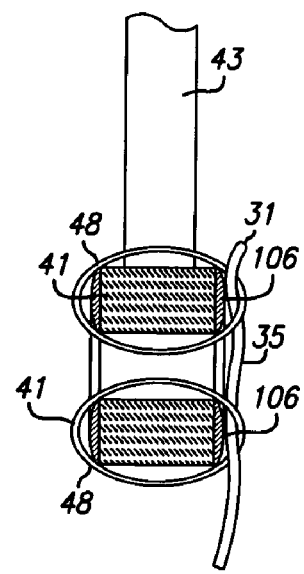
FIG. 2G is a partial cross-sectional view along the line 2E-J-2E-J of the area designated by the dotted lines in FIG. 2, depicting a stent eyelet having washers between the stent material and sutures.
Figure 2H:
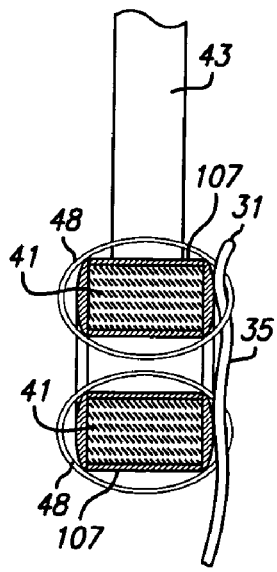
FIG. 2H is a partial cross-sectional view along the line 2E-J-2E-J of the area designated by the dotted lines in FIG. 2, depicting a stent eyelet having a coating between the stent material and sutures.
Figure 2I:
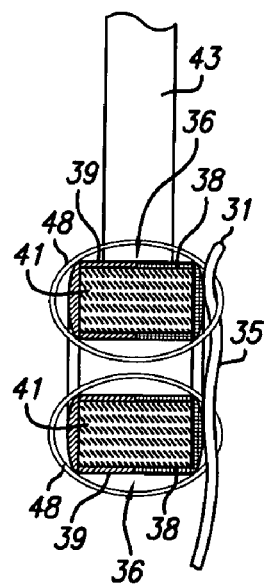
FIG. 2I is a partial cross-sectional view along the line 2E-J-2E-J of the area designated by the dotted lines in FIG. 2, depicting a stent eyelet having a two-piece grommet between the stent material and sutures.
Figure 2J:
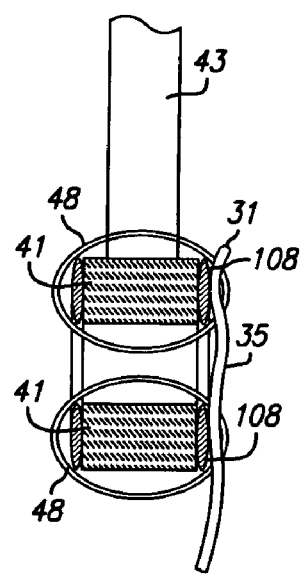
FIG. 2J is a partial cross-sectional view along the line 2E-J-2E-J of the area designated by the dotted lines in FIG. 2, depicting a stent eyelet having O-rings between the stent material and sutures.

Alternately, a large radius barrier may be provided between the attachment stent 40 connector eyelet 41 and the sutures. FIG. 2G shows an embodiment with an attachment stent 40 connector eyelet 41 with a washer 106 between the eyelet 41 and the sutures 48. The washer 106 has a round cross-section. FIG. 2H shows an attachment stent 40 connector eyelet 41 which has a coating 107 on it. The coating 107 provides a round cross-section. FIG. 2I shows an attachment stent 40 connector eyelet 41 with a grommet 36 between the eyelet 41 and the sutures 48. The grommet 36 consists of two rings 38, 39 and has a round cross-section. FIG. 2J shows an attachment stent 40 connector eyelet 41 with O-rings 108 between the eyelet 41 and the sutures 48. The O-rings 108 have a round cross-section. Each of the barriers provide a large radius against which the material of the suture 48 rests when it is pulled tight around the eyelet 41. The barriers may be made from any biocompatible material that will not degrade when the sutures 48 have a load placed on them.

In order to provide additional support for the main body component, additional stents may be provided. If sufficient healthy tissue exists, these stents may be additional attachment stents 40 intended to anchor the main body component in the patient's vasculature. Otherwise, these stents may be intended solely to provide support for the main body component 30 to preclude twisting, help deploy the main body component 30, or facilitate attachment of the limb portions. If the additional stents are attachment stents 40, the various attachment hooks 86 and methods described herein may be used (see FIGS. 1A-1H).

Figure 3A:
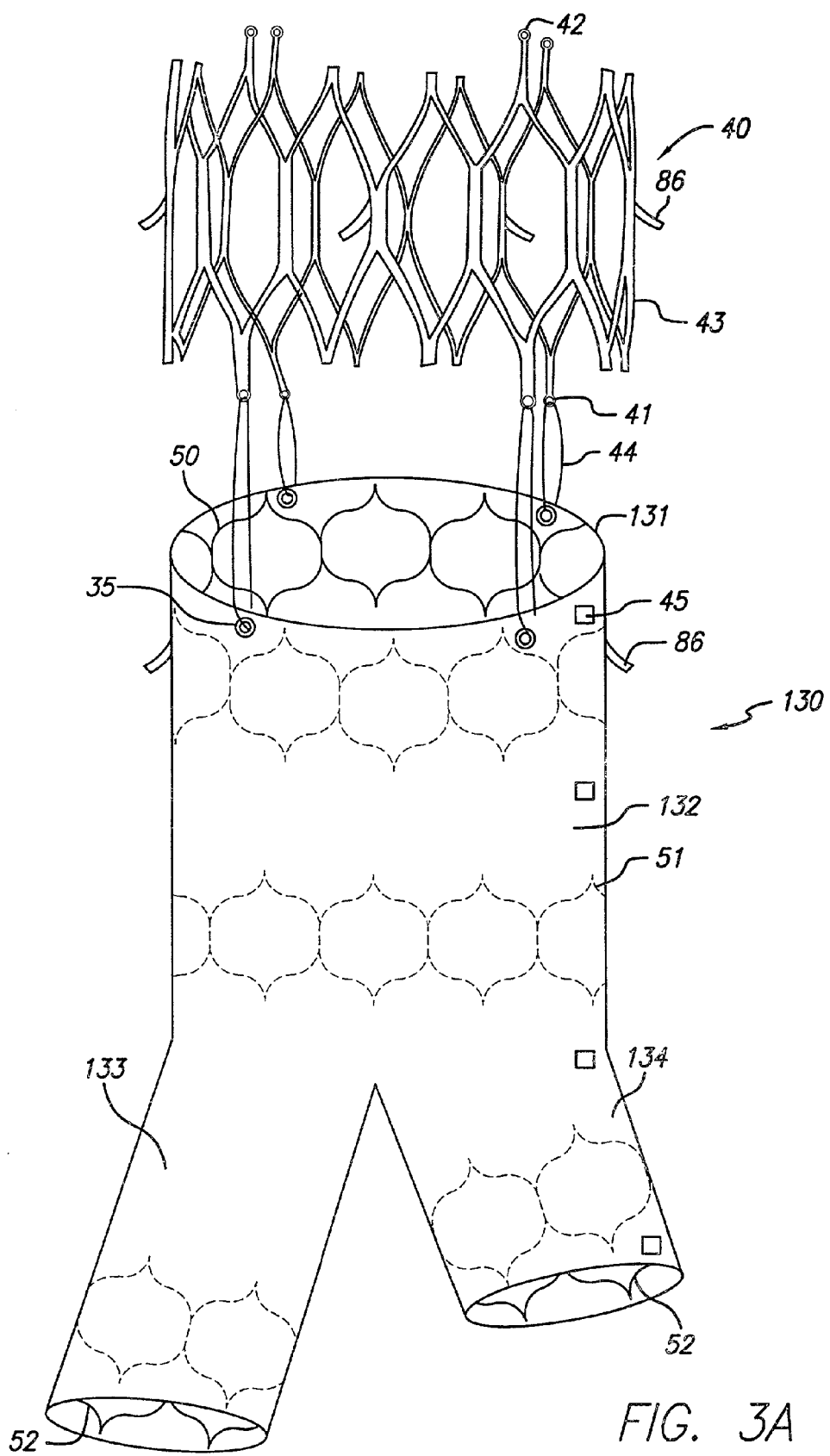
FIG. 3A is a perspective view, depicting the bifurcated endovascular graft main body component and attachment stent of one embodiment of the present invention with additional stents internal the graft material.

FIG. 3A shows an embodiment of a main body component 130 with additional stents 50, 51, 52, located inside the graft material at the neck 131, trunk 132, and limb support portions 133, 134 respectively. Hooks 86 may be provided if stent 50 is an attachment stent. Note that one limb support portion 134 is shorter than the other limb support portion 133. This facilitates a smaller delivery profile as the limb support portion stents 52 will not occupy the same axial space when the main body component 130 is compressed in a catheter sheath for delivery.

Although FIG. 3A depicts only four additional stents, it is contemplated that as many additional stents as desired may be provided. The longitudinal spacing of adjacent stents would be selected to provide a balance between longitudinal column strength and flexibility.

It is further contemplated that stent 50 may extend past the neck 131 of the main body component 130 such that it may penetrate the lumen wall. Stent 50 may be delivered and deployed separately from the main body component 130 using a stent delivery system known within the art. Delivering the stent 50 separate from the main body component 130 allows greater compression of the main body component 130 and, hence, facilitates using a smaller delivery system since there is not both stent and graft material to pack.

Figure 3B:
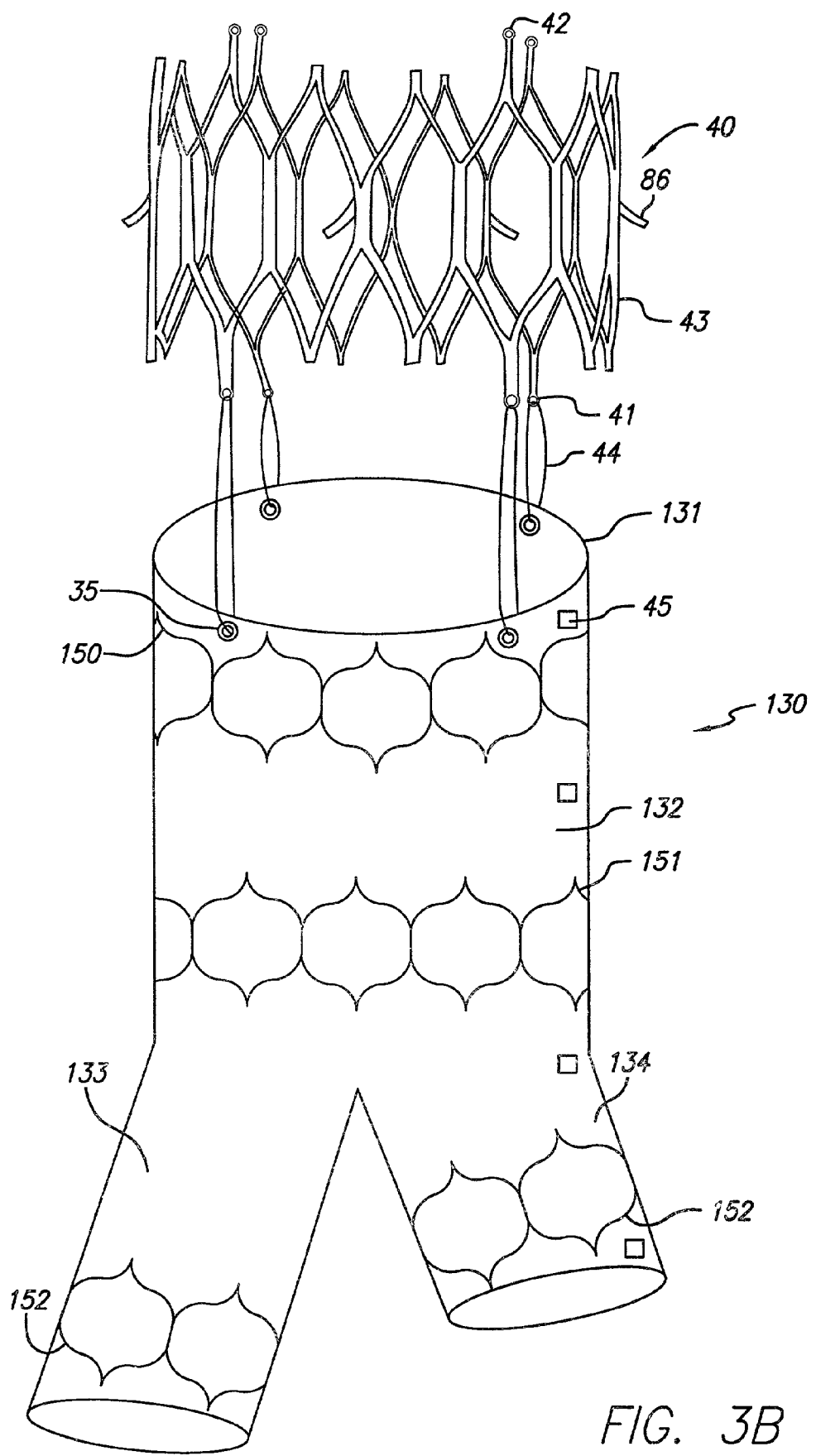
FIG. 3B is a perspective view, depicting the bifurcated endovascular graft main body component and attachment stent of another embodiment of the present invention with additional stents external the graft material.

FIG. 3B shows the additional stents 150, 151, 152 located external the graft material of the main body component 130. These external stents 150, 151, 152 would be delivered and deployed with the main body component 130.

Figures 3C, 3D:
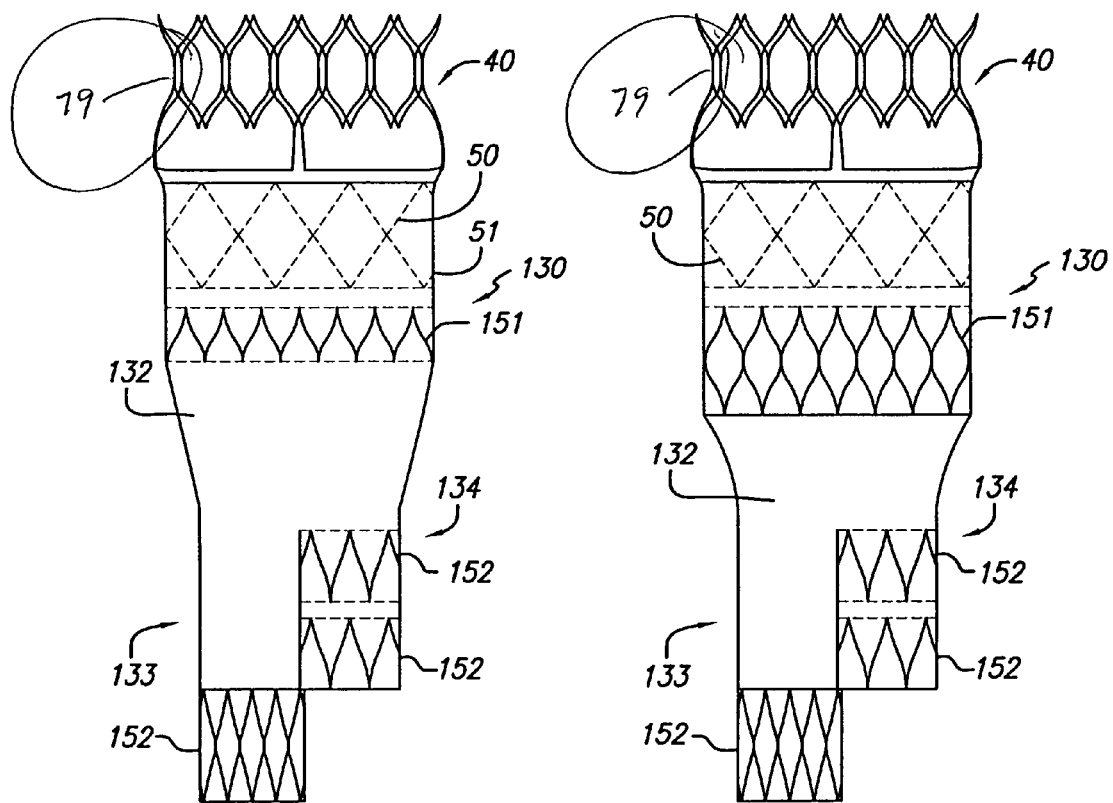
FIG. 3C is a perspective view, depicting the bifurcated endovascular graft main body component and attachment stent of another embodiment of the present invention with additional stents internal and external the graft material.
FIG. 3D is a perspective view, depicting a further embodiment of a bifurcated endovascular graft with internal and external stents.

The attachment 40 and additional stents 50, 51, 52, 150, 151, 152 may be of any type known within the art. It is contemplated that both internal and external stents may be provided depending upon the patient's vasculature and delivery package size restrictions. FIG. 3C shows a main body component 130 with an additional internal stent 50 at the neck, additional internal 51 and external 151 stents at the trunk 132, and additional external stents 152 at the limb support portions. As shown in FIG 3C, a sealing region is defined by three rings of half cell stents (12 cells each), two of which are positioned on the inside of the main graft component 130 and the third on the outside, although other combinations of inside and outside stents are contemplated. It is also contemplated that there be a 2-3 mm longitudinal space between the sealing stents of the main body and that the legs 133, 134, of the main body are sewn together. It is to be further noted that the fixation stent 40 is attached directly to the main body component 130 via tabs of graft (See FIGS. 1P-V and 1X-Z, for examples). Moreover, the main body graft component 130 can be formed so as to define a tapered profile in which the top of the graft is wider (has a larger inlet diameter) than the bottom of the graft (whose limb outlet diameters combined are less than the inlet diameter) as shown in FIGS. 3C-3E or a flared profile in which the bottom of the graft is larger than the top of the graft.

Turning to FIG. 3D, there is shown another embodiment of the main body component 130 embodying a sealing stent 50 sewn on the inside of the graft and a second stent 151 attached to the outside of the graft. The second stent 151 is configured to open the main body component 130 as well as to provide stability to the aortic system during implantation. The fixation stent 40 is attached to the main graft component 130 using tabs of graft and the main graft component can otherwise lack scalloped sections to thereby reduce redundancy of material at the top of the graft 130.

Figure 3E:
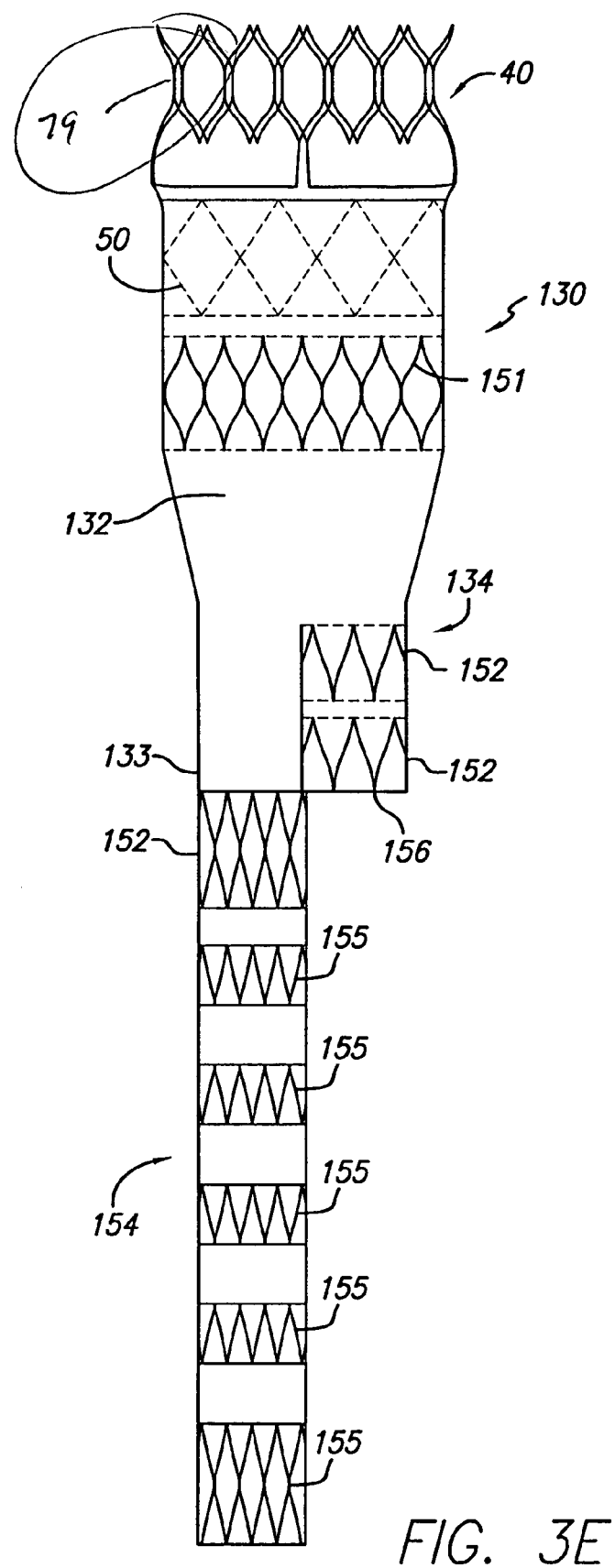
FIG. 3E is a perspective view, depicting the bifurcated graft shown in FIG. 3D mated with a limb component.

With respect to FIG. 3E, there is shown a limb component 154 attached to a main body component 130. In a preferred embodiment, the legs 133, 134 can have a diameter on the order of 13 mm. One leg 134 can be supported by a pair of stent structures 152 for added stability for receiving a guidewire or other medical devices. Additionally, a radiopaque marker 156 can be wrapped about an apex of the stent structure 152 supporting the leg 134. The limb component 154 is shown as being flared but can also be tapered for a particular application. Moreover, half or full cell supporting stents 155 are contemplated to be spaced along a length of the limb component 154 in a manner providing the limb component with a balance between longitudinal column strength and bending flexibility without buckling or kinking of the graft component. In an alternate embodiment, the supporting stents along the mid-portion of the limb are not used.

When the additional stents 50, 51, 52 are located inside the graft material, the inward bend of the proximal and distal ends may interfere with medical devices such as guidewires, catheters, or limb components subsequently introduced into the lumen formed by the stent. FIGS. 4A-4B and 5A-5B show methods for precluding this interference.

Figures 4A, 4B:
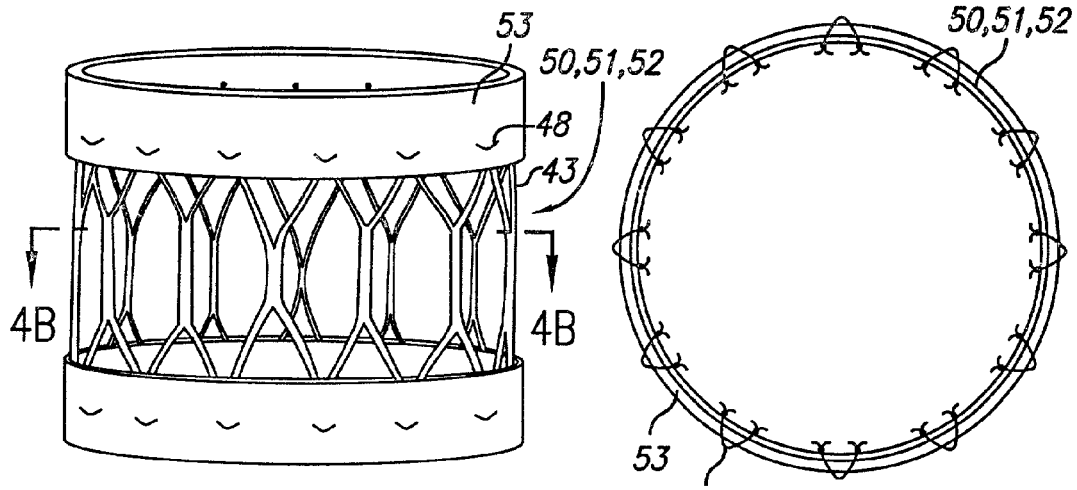
FIG. 4A is a perspective view, depicting a stent of one embodiment of the present invention with double-layer graft end cuffs attached over the proximal and distal ends.
FIG. 4B is a cross-sectional view along line 4B-4B of FIG. 4A.

As shown in FIGS. 4A-4B, a graft end cuff 53 consisting of two layers which form an annular space, may be fitted over the proximal and distal ends of the stent 50, 51, 52. With the ends of the stent 50, 51, 52 encased in the annular space, any inward bend of the stent struts 43 is precluded from interfering with subsequent devices or limbs inserted within the lumen formed by the stent 50, 51, 52. The cuff 53 is held in place by sutures 48 which attach the cuff 53 to the encased stent 50, 51, 52 proximal and distal ends respectively.

Figures 5A, 5B:
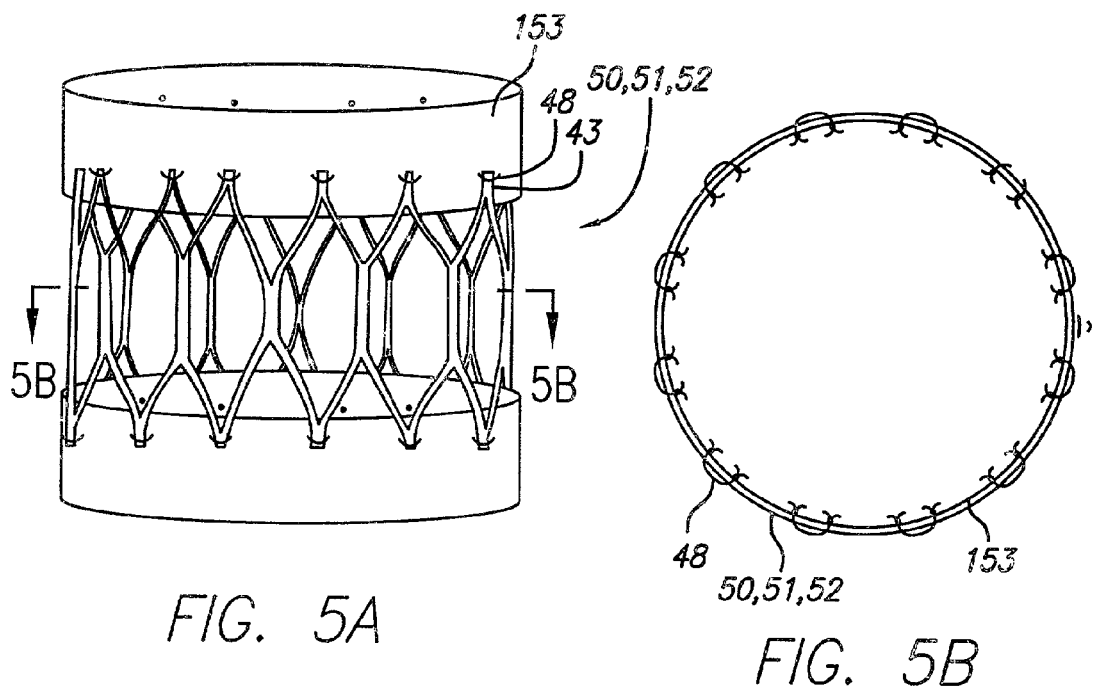
FIG. 5A is a perspective view, depicting a stent of another embodiment the present invention with single-layer graft end cuffs attached inside the proximal and distal ends.
FIG. 5B is a cross-sectional view along line 5B-5B of FIG. 5A.

Alternately, as shown in FIGS. 5A-5B, the graft end cuff 153 may consist of a single layer attached inside the proximal and distal ends of the stent 50, 51, 52 by sutures 48. The inner surface of the stent 50, 51, 52 proximal and distal ends is covered, thereby retaining the patency of the lumen within the stent 50, 51, 52. The outer surface of the stent 50, 51, 52 is left exposed, thereby providing radial force and structural support necessary for adhesion to the vessel within which it is implanted.

The graft cuffs 53, 153 may be made of graft material, such as PET (Dacron®) or PTFE, or any functionally capable plastic. In a preferred embodiment the graft cuffs 53, 153 are made of woven polyester graft material attached to the stent 50, 51, 52 with 3-OT polyester sutures. It is contemplated that these methods may be applied to stents located within the main body component or limb components, as well as whenever it is desired to retain the patency of a human vessel or implant conduit.

In order to facilitate greater compression of stents and hence, a smaller delivery package, the stents may be configured so as to offset longitudinally the endovascular graft connection points. Since the connection point is traditionally wider in the circumferential direction than the stent struts to which it is attached, it can limit the size to which the stent can be compressed.

Figure 6A:
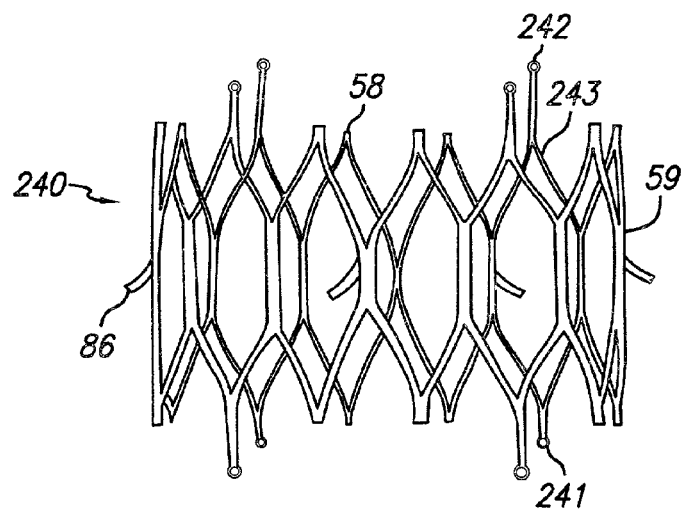
FIG. 6A is a perspective view, depicting one embodiment of an attachment stent of the present invention with longitudinally offset connection points.
Figure 6B:
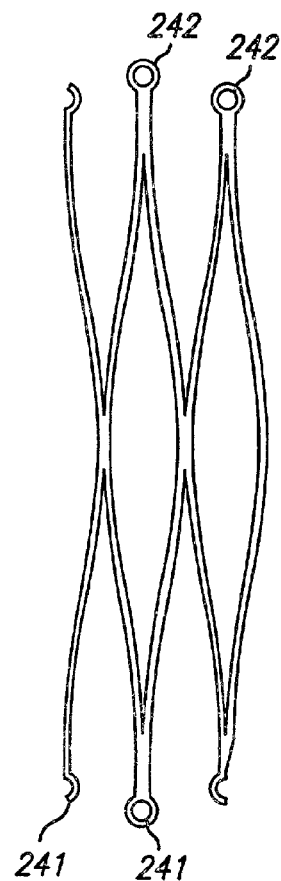
FIG. 6B is an enlarged view, depicting offsetting connecting points.

FIG. 6A depicts an attachment stent 240 which defines one aspect of the present invention. The connector eyelets 241 and loading eyelets 242 are circumferentially-wider than the rest of the stent struts 243. Note that the connector eyelets 241 and loading eyelets 242 are offset in the longitudinal direction with two of four connector eyelets 241 shorter than the others and two of four loading eyelets 242 shorter that the others. When the stent 240 is collapsed, only two of the connector eyelets 241 and two of the loading eyelets 242 occupy the same longitudinal position, thereby allowing greater compression of the stent 240. FIG. 6B is provided to highlight the offsetting of connecting points or atraumatic structures.

Figure 7A:
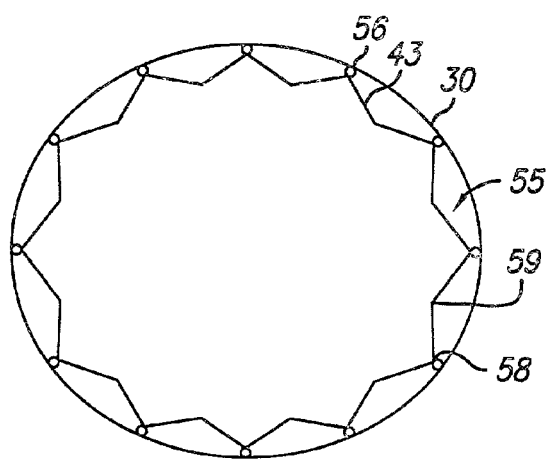
FIG. 7A is a cross-sectional top view, depicting the contact points between a stent of the present invention having flat bulbous end portions and the graft material.
Figure 7B:
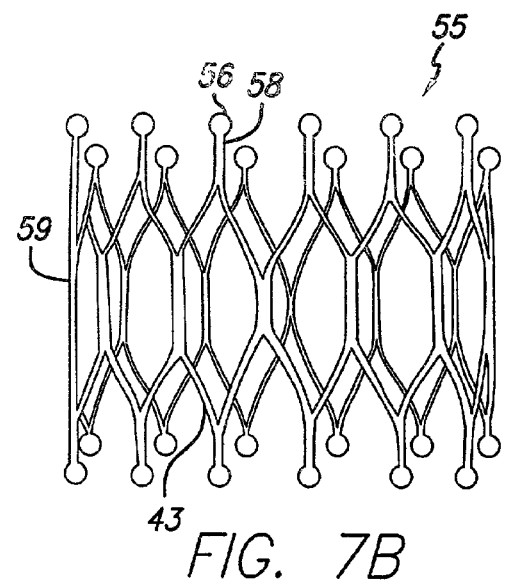
FIG. 7B is a perspective view, depicting a stent of one embodiment of the present invention having longitudinally offset flat bulbous end portion connection points.
Figure 8A:
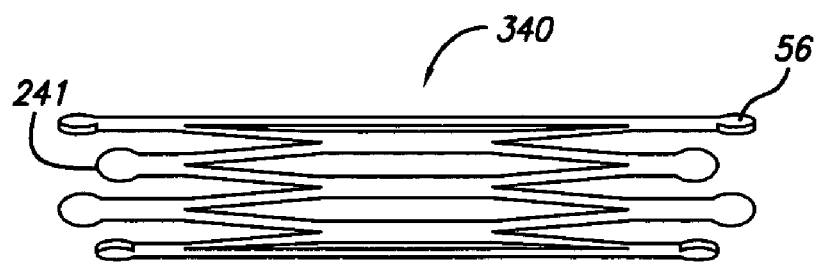
FIG. 8A is a perspective view, depicting an attachment stent of the present invention in a compressed state with longitudinally offset connection points.

As shown in FIGS. 7A and 7B, in order to minimize wear at the contact point between a stent and the lumen wall or graft material, flat bulbous or wide areas 56 may be located at the ends of the stent such that at least one strut or apex at either end of the stent is larger than the strut thickness for spreading the point-load at the end of the stent over a wider area. FIG. 7A depicts the contact points between a typical support stent 55 having flat bulbous end portions 56 and the graft material of the main body component 30. These flat bulbous end portions 56 are circumferentially-wider than the other stent struts 43. FIG. 7B depicts the support stent 55 flat bulbous end portions 56 offset longitudinally such that only one half of these circumferentially wide areas occupy the same axial location when the stent 55 is compressed for delivery. FIG. 8A depicts an attachment stent 340 in a compressed state showing how the longitudinally-offset connector eyelets 241 at the distal end and the longitudinally-offset flat bulbous end portions 56 at the proximal end facilitate a reduced delivery profile.

Figure 8B:
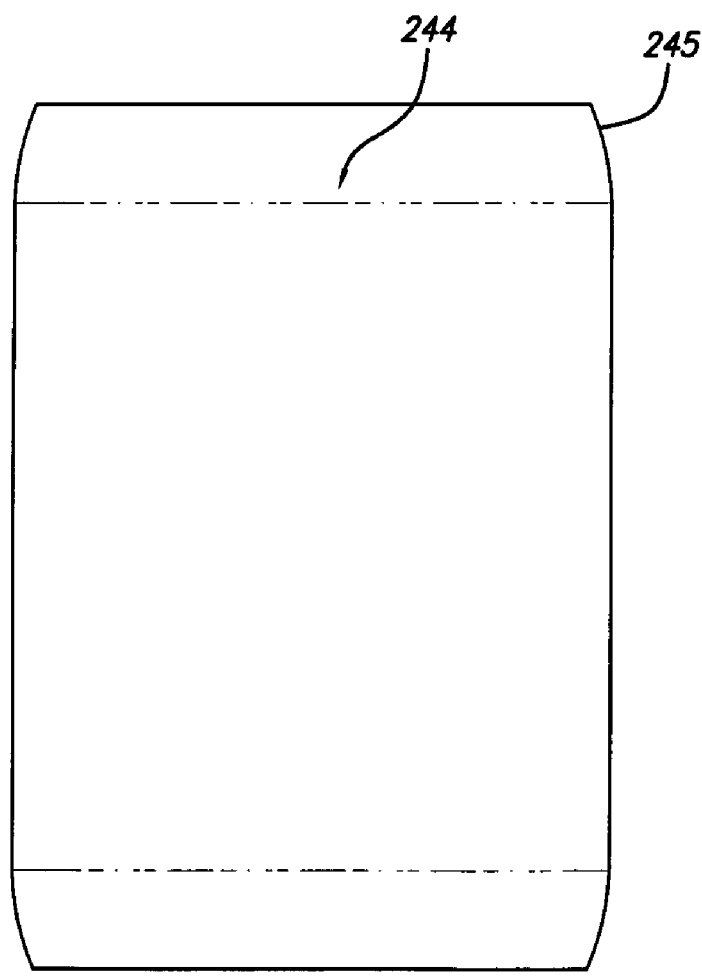
FIG. 8B is an elevational view, depicting a tubular structure with rounded ends used to form a stent having atraumatic ends.

An alternate method of minimizing wear at the contact point between a stent and the lumen wall or graft material is to either grind the stent with a radial radius around the circumference of the strut 43 ends or, if the stent is laser cut from a Nitinol tube 244, grind the ends 245 of the tube prior to cutting the stent (see FIG. 8B). The contact point between the stent and the lumen wall or graft material is the tangent point of the radius of ends 245. By radiusing or chamfering the ends of the tube the stent is made from or radiusing or chamfering the ends of the stent after cutting the stent, there is a smooth surface presented against the graft or vessel into which the stent is placed.

As shown in FIG. 6A and 7B, a reduced profile delivery package may be facilitated by tapered stent struts 243, 43. By making the thickness of the stent struts 243, 43 smaller in the wishbone area 58 than in the cell joint area 59, the volume of the collapsed stent 240, 55 may be decreased.

Figure 9:
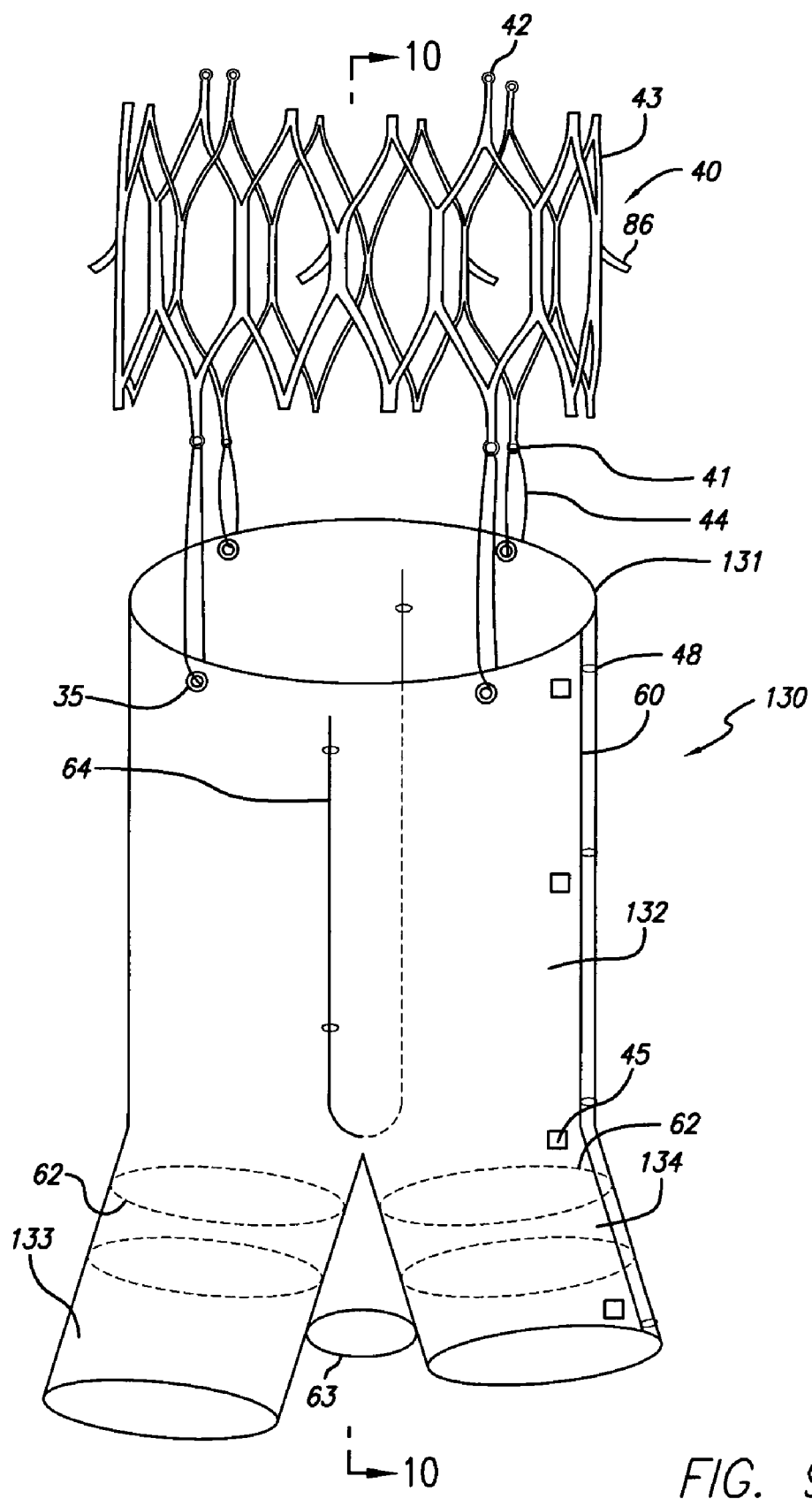
FIG. 9 is a perspective view, depicting an alternate embodiment of a bifurcated endovascular graft main body component and attachment stent of the present invention with wire and suture supports.
Figure 10:
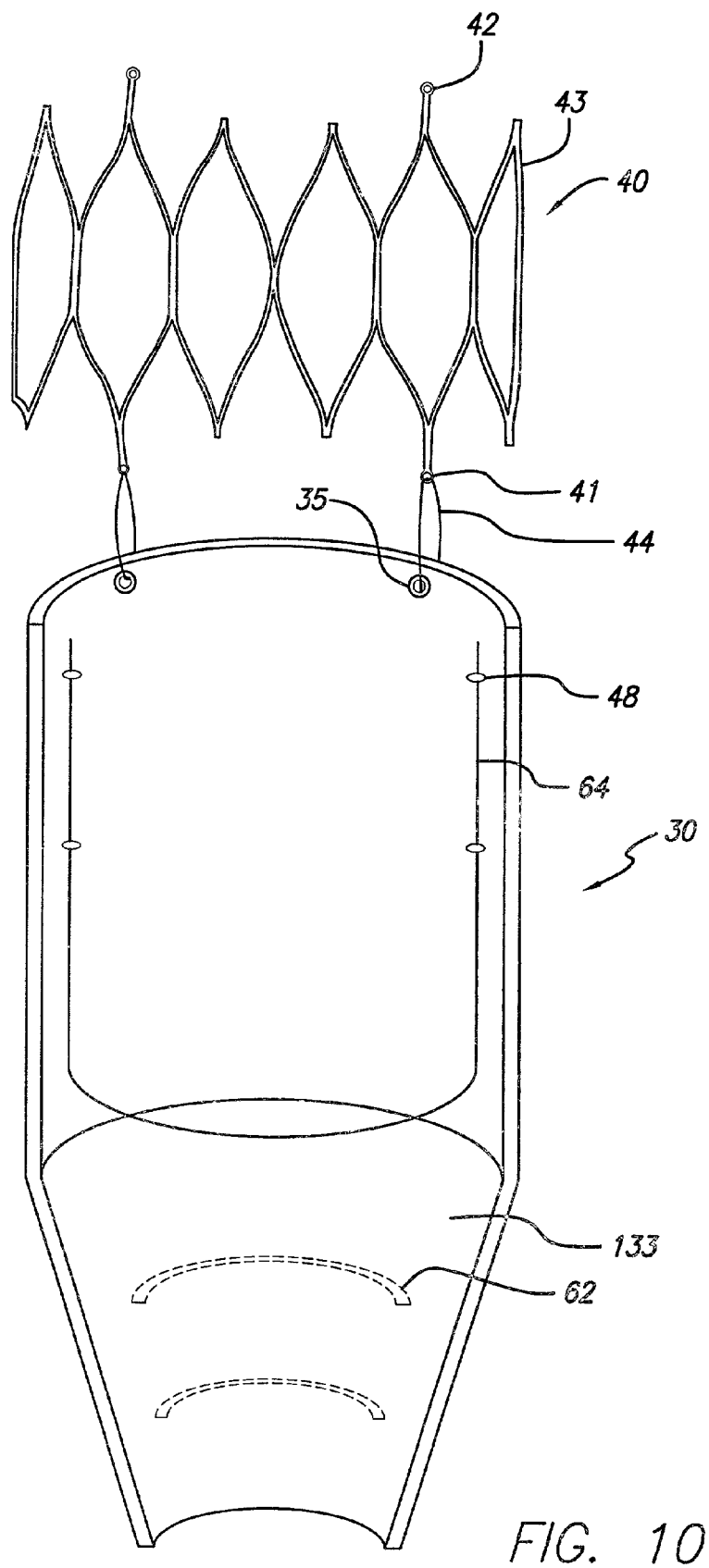
FIG. 10 is a cross-sectional view along line 10-10 of FIG. 9 depicting an anti twist wire attached between the limb support portions of a bifurcated endovascular graft main body component.

Alternately, sutures and wires may provide additional support for the main body component 30. FIG. 9 depicts an embodiment of a main body component 130 with a stiffening wire 60, limb support portion suture loops 62, and limb support portion suture tether 63. The stiffening wire 60 is attached to the main body component 130 graft material by sutures 48 and provides support for a main body component 130 which is not fully-stented, having only an attachment stent 40. The suture loops 62 are attached inside the graft material of each limb support portion 133, 134 and facilitate attachment of the limb components by maintaining an open docking section for the limbs. The suture tether 63 connects the two limb support portions 133, 134 together and facilitates catheterization of the contra-lateral limb support portion 134 by keeping it steady. For instance, if the main body component 130 is only partially-deployed by a delivery catheter (not shown) whereby only the shorter contra-lateral limb support portion 134 is freed, the delivery catheter maintains control of both the ipsi-lateral limb support portion 133 and contra-lateral limb support portion 134. Catheterization of the contra-lateral limb support portion 134 by a second catheter (not shown) is thereby facilitated. Additional support may be achieved by an anti-twist wire 64 that is attached to the main body component 30 graft material. As shown in FIG. 10, the anti-twist wire 64 has the shape of the letter "U" with the open end of the "U" pointing toward the attachment stent 40 and the bottom of the "U" running through the crotch between the limb support portions 133, 134, such that the ends of the wire 64 are attached to opposite sides of the graft material by sutures 48. The presence of the anti-twist wire 64 resists twisting of the main body component 30 when its distal end is not supported by stents or attached within the patient's vasculature and thereby, facilitates attachment of the limb components.

Figure 11A:
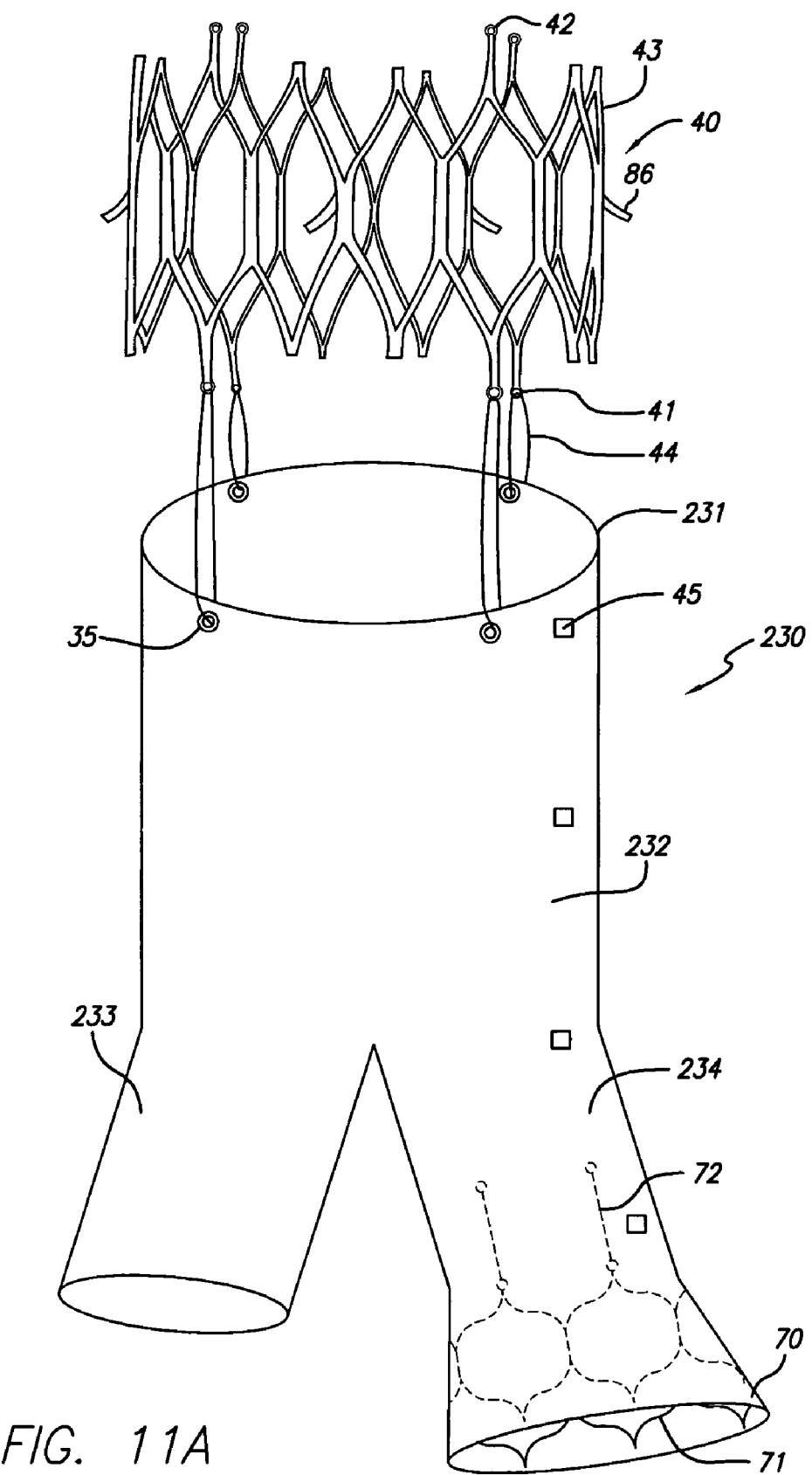
FIG. 11A is a perspective view, depicting an alternate embodiment of a bifurcated endovascular graft main body component and attachment stent of the present invention with a bell-bottom limb support portion having a stent internal to the graft material.
Figure 11B:
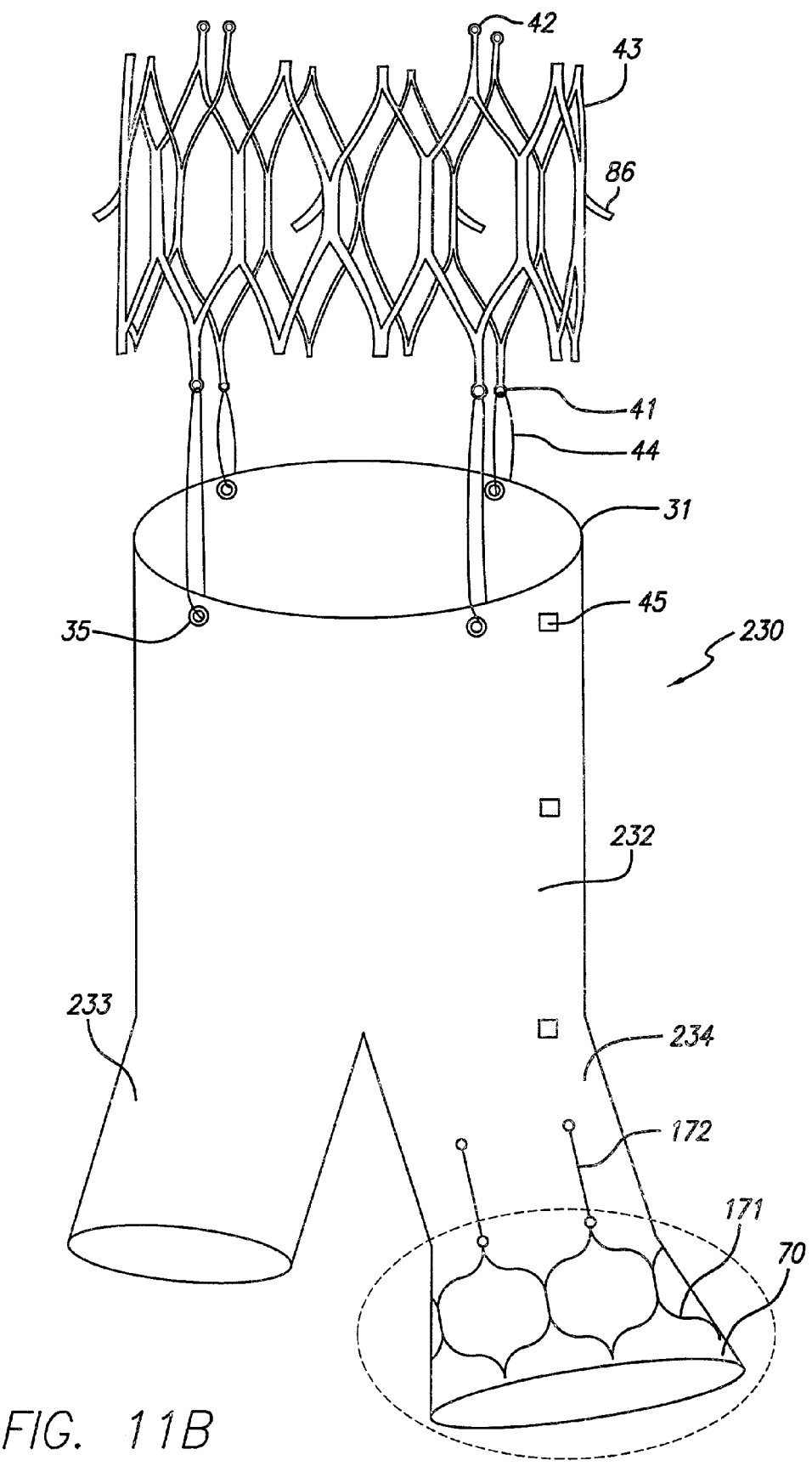
FIG. 11B is a perspective view, depicting an alternate embodiment of a bifurcated endovascular graft main body component and attachment stent of the present invention with a bell-bottom limb support portion having a stent external the graft material.

Catheterization of the contra-lateral limb support portion 134 is facilitated further by a main body component 130 having a contra-lateral limb support portion with a "bell-bottom" shape. FIG. 11A depicts an embodiment of a main body component 230 with a "bell-bottom" limb support portion 234 with a self-expanding "bell-bottom" stent 71 at the distal end 70. If sufficient healthy tissue exists, this stent 71 may be an attachment stent intended to anchor the "bell-bottom" limb support portion 234 in the patient's vasculature. Otherwise, this stent 71 may be intended solely to provide support for the "bell-bottom" limb support portion 234 to facilitate catheterization. Note that some of the wires that compose the "bell-bottom" stent 71 extend proximally into the limb support portion 234. This "bell-bottom" stent extension 72 ensures a sufficient docking section for the limb component if the limb support portion 234 becomes displaced due to the vessel shape. Even if the limb support portion 234 is bent, the added rigidity from the stent extension 72 ensures that the bending will occur proximal of this area, thereby maintaining a rigid portion for attachment of the limb component. The only limitation of the length of this extension 72 is the length of the limb support portion 234. The "bell-bottom" stent 71 may be of any type known within the art. In the embodiment depicted in FIG. 11A the "bell-bottom" stent 71 is located inside the graft material. FIG. 11B shows an alternate embodiment of the main graft component 230 with the "bell-bottom" stent 171 located external the graft material. It is contemplated that both internal and external stents 71, 171 may be provided depending upon the patient's vasculature and delivery package size restrictions.

Figure 11C:
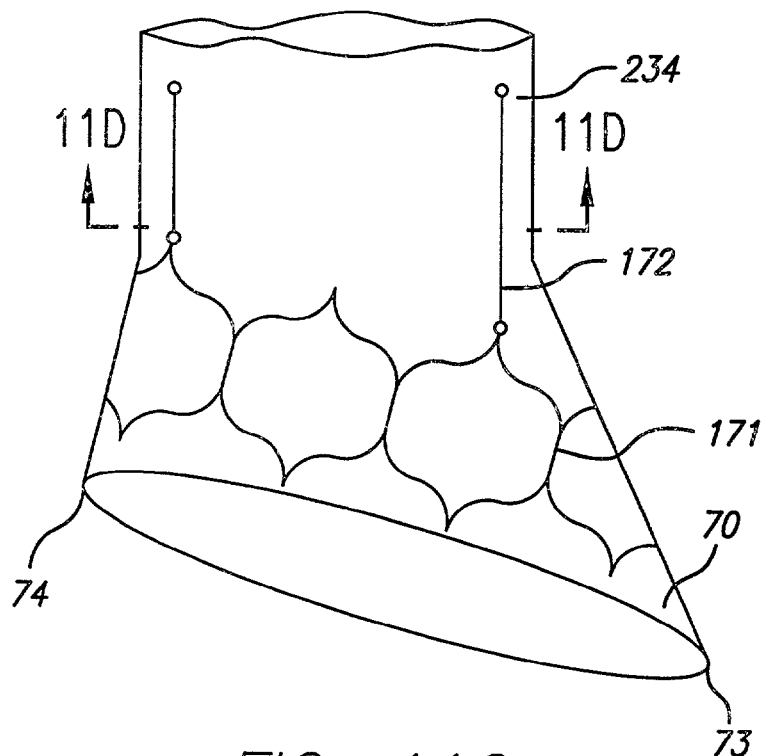
FIG. 11C is a partial view of the area designated by the dotted lines in FIG. 11B, depicting an alternate embodiment of the bell-bottom limb support portion.
Figure 11D:
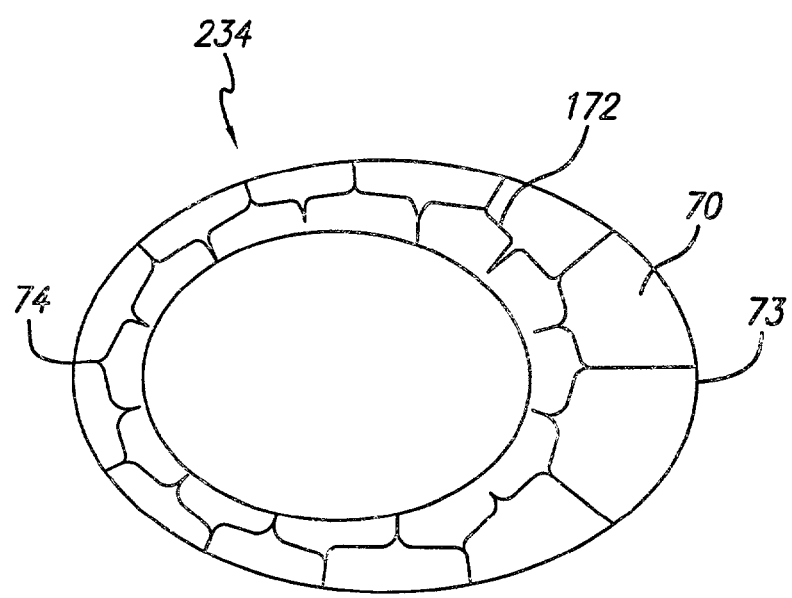
FIG. 11D is a cross-sectional view along the line 11D-11D in FIG. 11C.

FIGS. 11C and 11D depict an alternate embodiment of the "bell-bottom" limb support portion 234 that provides an increased target surface area for catheterization. The "bell-bottom" limb support portion 234 is modified by making the distal edge opposite the other limb 73 significantly longer or larger in surface area and the profile of the distal end 70 oval.

By maintaining the radiopaque markers 45 located along the contra-lateral side in a straight row when the main body component 30 is compressed, the attachment stent 40 and main body component 30 may be packed to achieve a smaller profile while still allowing proper orientation upon deployment. Using fluoroscopy, the technician can maneuver the delivery system until a straight row of markers 45 is observed on the contra-lateral side of the body lumen, indicating that the main body component 30 is properly aligned before it is deployed. After deployment, the row of radiopaque markers 45 allow the technician to position additional hardware, such as a delivery system for additional stents or limb components, relative to the neck 31, trunk 32, bifurcation, and contra-lateral limb support portion 34. It is contemplated that radiopaque markers 45 may be placed in a row along any graft that requires orientation inside the vasculature prior to deployment.

Figure 12:
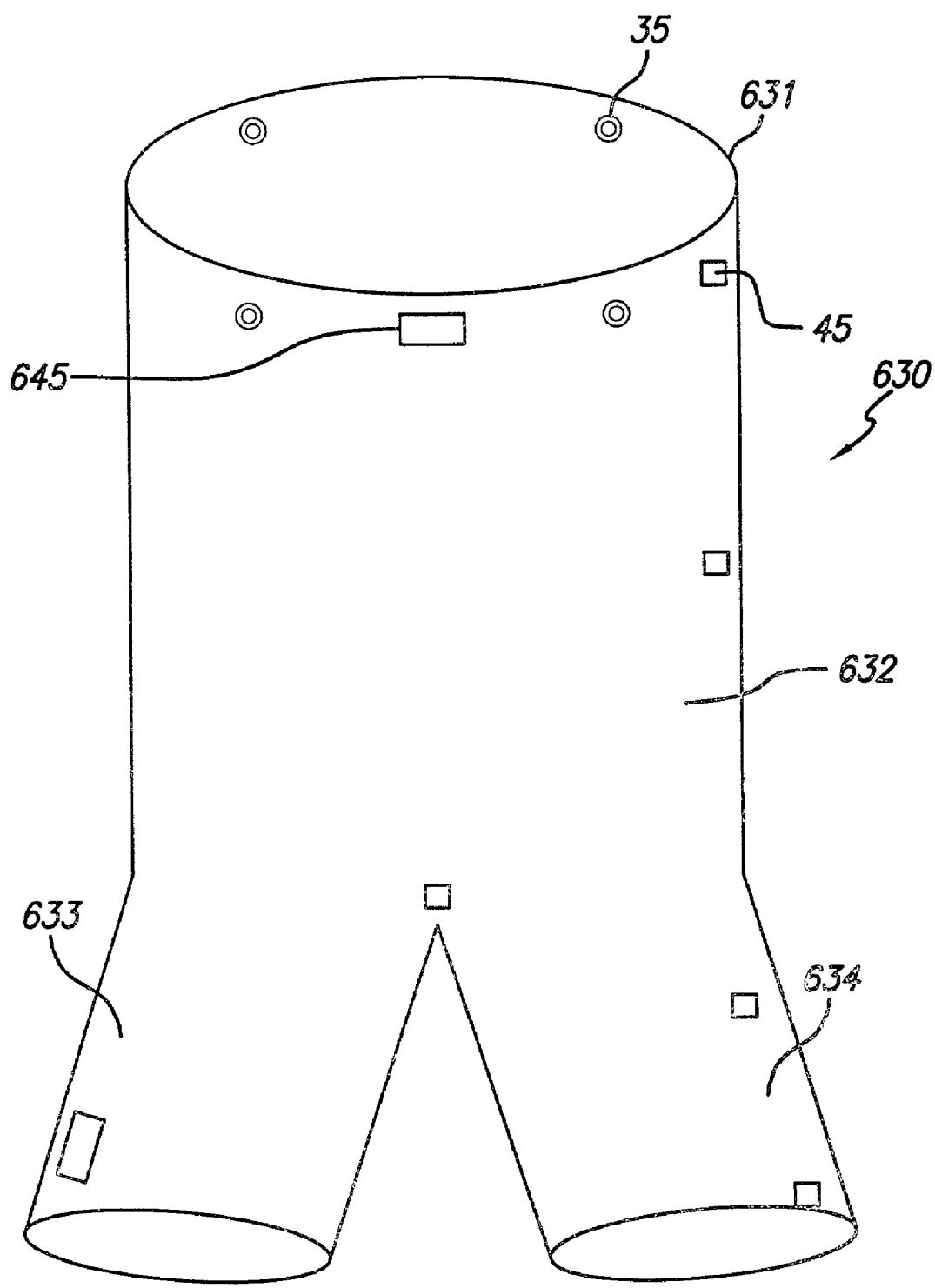
FIG. 12 is a perspective view of an alternate embodiment of the bifurcated endovascular graft main body component depicted in FIG. 1 with the small radiopaque markers located along the contra-lateral side and at the bifurcation and large radiopaque markers located at the neck and the distal end of the ipsi-lateral limb support portion.

Alternately, additional radiopaque markers may be placed on the main body component 30 to better facilitate deployment as well as subsequent deployment of the ipsi-lateral limb component. FIG. 12 shows a main body component 630 with small radiopaque markers 45 along the contra-lateral side at the neck 631, trunk 632, below the bifurcation, and the distal end of the ipsi-lateral limb support portion 634. Additionally, there is a small radiopaque marker 45 at the bifurcation and large radiopaque markers 645 at the center of the neck and at the distal end of the ipsi-lateral limb support portion 633. Packing the main body component (FIG. 1) and attachment stent 40 so as to maintain the straight row of the small radiopaque markers 45 on the contra-lateral side facilitates proper orientation of the main body component 30 before deployment. The additional radiopaque markers 45, 645, of FIG. 12, facilitate more efficient placement of subsequent components, such as additional stents or the limb components, by providing additional landmarks on the main body component 630. The larger size of the additional neck and ipsi-lateral limb support portion 633 radiopaque markers 645 facilitate differentiation from the smaller radiopaque markers 45 on the contra-lateral side when the main body component 630 is packed in the delivery system. In a preferred embodiment, the small radiopaque markers 45 are 1 millimeter platinum coils, the large radiopaque marker 645 at the neck is a 2.5 millimeter platinum coil, and the large radiopaque marker 645 at the distal end of the ipsi-lateral limb support portion 633 is a platinum coil of 2.5 to 4 millimeters.

Figure 13:
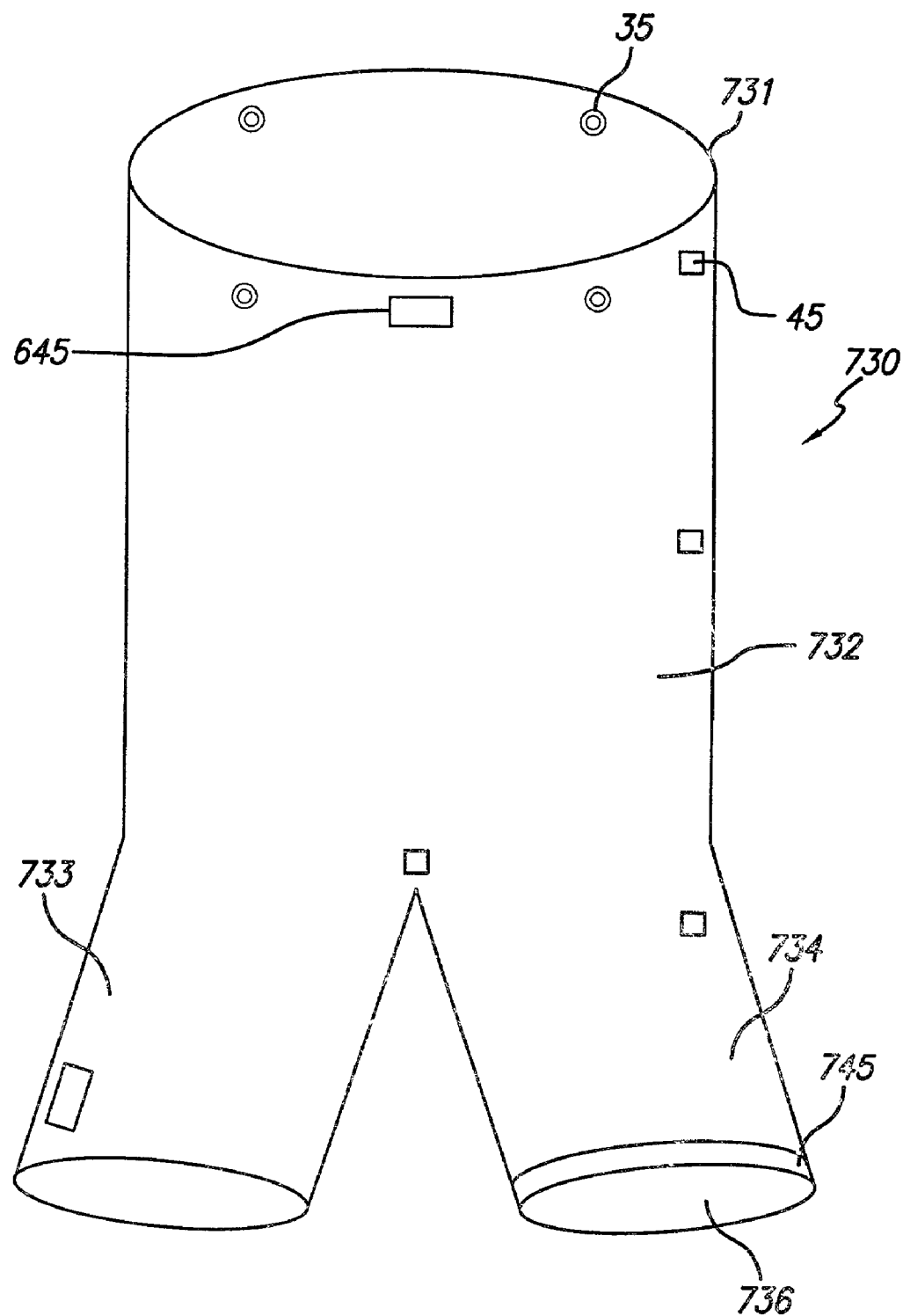
FIG. 13 is a perspective view of an alternate embodiment of the bifurcated endovascular graft main body component depicted in FIG. 12 with a continuous radiopaque band at the distal end of the contra-lateral limb support portion.

In another alternate embodiment, a continuous radiopaque band facilitates subsequent procedures, such as insertion of a guidewire or insertion and deployment of the contra-lateral limb component. FIG. 13 shows a main body component 730 with a radiopaque band 745 around the distal edge of the contra-lateral limb support portion 734. Under fluoroscopy, the radiopaque band 745 provides better feedback than conventional markers regarding the relative position of inserted hardware with respect to the contra-lateral limb support portion opening 736 of the main body component 730 as the opening 736 will appear on a fluoroscope screen as a circle or oval whereas a conventional marker just indicates a point around the opening. In a preferred embodiment, the continuous radiopaque band 745 is composed of radiopaque ink applied about the circumference of the contra-lateral limb support portion 734. In another embodiment, the continuous band can be a radiopaque thread sewn about the circumference of the opening 736. A continuous radiopaque band 745 may also be utilized on the ipsi-lateral limb support portion 733. It is contemplated that radiopaque ink may be utilized in other places on the graft components as orientation and location markings. The radiopaque ink markings take up less volume thus allowing the graft components to be packed into a smaller profile delivery system.

Thus, it will be apparent from the foregoing that, while particular forms of the invention have been illustrated and described, various modifications can be made without departing from the spirit and scope of the invention. For example, the main and limb components can each be generally tubular, flared, bifurcated or trifurcated. Accordingly, it is not intended that the invention be limited, except as by the appended claims.

What is claimed is:

1. An endovascular graft for treating vasculature, comprising:
 a graft component including a first leg portion and a second leg portion, the first leg portion being attached along its length to the second leg portion, the graft component having an opening and a plurality of structures extending longitudinally beyond the opening, the opening having an opening circumference;
 an expandable frame;
 an attaching structure that attaches the expandable frame to the graft component by engaging at least one of the plurality of structures extending longitudinally beyond the opening; and
 an anchoring structure that anchors the expandable frame to the lumen wall;
 wherein the expandable frame is longitudinally separated from the graft component;
 wherein the attaching structure attaches the expandable frame to the graft component at discrete locations on the graft component so that less than an entirety of a graft circumference is affixed to the attaching structure and wherein the opening of the graft component lacks other structure supporting a totality of the opening circumference; and
 wherein at least one of the plurality of structures extending beyond the opening is in the form of a tab which is folded over a portion of the attaching structure.

2. The graft of claim 1, wherein the tab is formed as part of the graft component.

3. The graft of claim 1, wherein the tab is formed by cutting one of the plurality of structures extending beyond the opening and folding the graft component material back.

4. The graft of claim 1 wherein the tab is reinforced by sutures.

5. The graft of claim 1, wherein the graft component is bifurcated.

6. The graft of claim 1, wherein the expandable frame is self-expanding.

7. The graft of claim 1, wherein the anchoring structure comprises a hook or barb.

8. The graft of claim 7, wherein the hook or barb is curved.

9. The graft of claim 7, wherein the hook or barb is tapered.

10. The graft of claim 7, wherein the hook or barb is bidirectional.

11. The graft of claim 7, the hook or barb further comprising a tail.

12. The graft of claim 7, the hook or barb cut at the edge of a stent strut of the anchoring structure.

13. The graft of claim 7, the hook or barb located near the junction of stent struts of the anchoring structure.

14. The graft of claim 1, the graft component further comprising reinforcing structures.

15. The graft of claim 14, wherein the reinforcing structures are self-expanding.

16. The graft of claim 14, wherein a reinforcing structure is in the form of a stent.

17. The graft of claim 14, wherein a reinforcing structure is on an exterior of the graft component.

18. The graft of claim 14, wherein a reinforcing structure is on an interior of the graft component.

19. The graft of claim 18, wherein a reinforcing structure comprises a hook or barb.

20. The graft of claim 19, wherein the hook or barb is curved.

21. The graft of claim 19, wherein the hook or barb is tapered.

22. The graft of claim 19, wherein the hook or barb is bidirectional.

23. The graft of claim 19, the hook or barb cut at the edge of a stent strut of the reinforcing structure.

24. The graft of claim 19, the hook or barb located near the junction of stent struts of the reinforcing structure.

25. The graft of claim 1, further comprising a plurality of radiopaque markers.

26. The graft of claim 1, the expandable frame further including endpoints that are larger than a strut thickness of the expandable frame.

27. The graft of claim 1, further comprising a system of variable sized radiopaque markers attached to the graft component.

28. The graft of claim 1, further comprising stent structures attached to both an inside surface and an outside surface of the graft component.

29. The graft of claim 1, further comprising a plurality of reinforcing structures attached to the graft component, wherein the plurality of reinforcing structures and the expandable frame are each spaced longitudinally so that the reinforcing structures and expandable frame are non-overlapping.

* * * * *